(12) United States Patent
Moyle et al.

(10) Patent No.: US 7,741,106 B2
(45) Date of Patent: Jun. 22, 2010

(54) SENSORS FOR BIOMOLECULAR DETECTION AND CELL CLASSIFICATION

(76) Inventors: William R. Moyle, 952 River Rd., Piscataway, NJ (US) 08854; Russell C. Scaduto, Jr., 314 Scout La., Hummelstown, PA (US) 17036

( * ) Notice: Subject to any disclaimer, the term of this patent is extended or adjusted under 35 U.S.C. 154(b) by 286 days.

(21) Appl. No.: 12/148,243

(22) Filed: Apr. 17, 2008

(65) Prior Publication Data

US 2009/0023148 A1 Jan. 22, 2009

(51) Int. Cl.
*C12M 1/34* (2006.01)
*C12M 3/00* (2006.01)
(52) U.S. Cl. ..................... 435/287.2; 435/6
(58) Field of Classification Search ............. 435/6, 435/287.1–287.3, 288.5, 288.7; 204/613, 204/614, 466
See application file for complete search history.

(56) References Cited

U.S. PATENT DOCUMENTS

| | | | | |
|---|---|---|---|---|
| 4,978,503 A | * | 12/1990 | Shanks et al. | 422/58 |
| 5,234,566 A | * | 8/1993 | Osman et al. | 204/403.06 |
| 5,567,290 A | * | 10/1996 | Vadgama et al. | 205/778 |
| 6,120,662 A | * | 9/2000 | Edwards et al. | 204/400 |
| 6,238,909 B1 | * | 5/2001 | Choong et al. | 435/287.2 |
| 6,387,707 B1 | * | 5/2002 | Seul et al. | 436/164 |
| 6,703,203 B2 | * | 3/2004 | Shao et al. | 435/6 |
| 7,615,369 B2 | * | 11/2009 | Lin et al. | 435/287.1 |
| 2003/0201194 A1 | * | 10/2003 | Heller et al. | 205/777.5 |

* cited by examiner

*Primary Examiner*—Walter D Griffin
*Assistant Examiner*—Shanta G Doe
(74) *Attorney, Agent, or Firm*—Richard R. Muccino

(57) ABSTRACT

A sensor device is provided for detecting an analyte in a sample in which an analyte is bound to a detection reagent to form a bound complex. The device comprises (a) a sample (5) comprising an ionic analyte and a detection reagent in a conductive fluid, wherein the detection reagent has a net charge different from the analyte; (b) a first permeable polymeric hydrogel plate (3) and a first spacer plate (8), which plates provide a compartment for the sample; (c) an anode (1) juxtaposed to the outside of the first hydrogel plate and not in contact with the sample; (d) a cathode (9) juxtaposed to the outside of the first spacer plate and not in contact with the sample; (e) a voltage generator (10) to apply an electric potential to the anode and cathode; and (f) a detector (11). The bound complex formed from the analyte and detection reagent is detected by the detector because the bound complex has a charge that causes it to migrate in a direction opposite from that of the unbound analyte when the electric potential is applied.

19 Claims, 24 Drawing Sheets

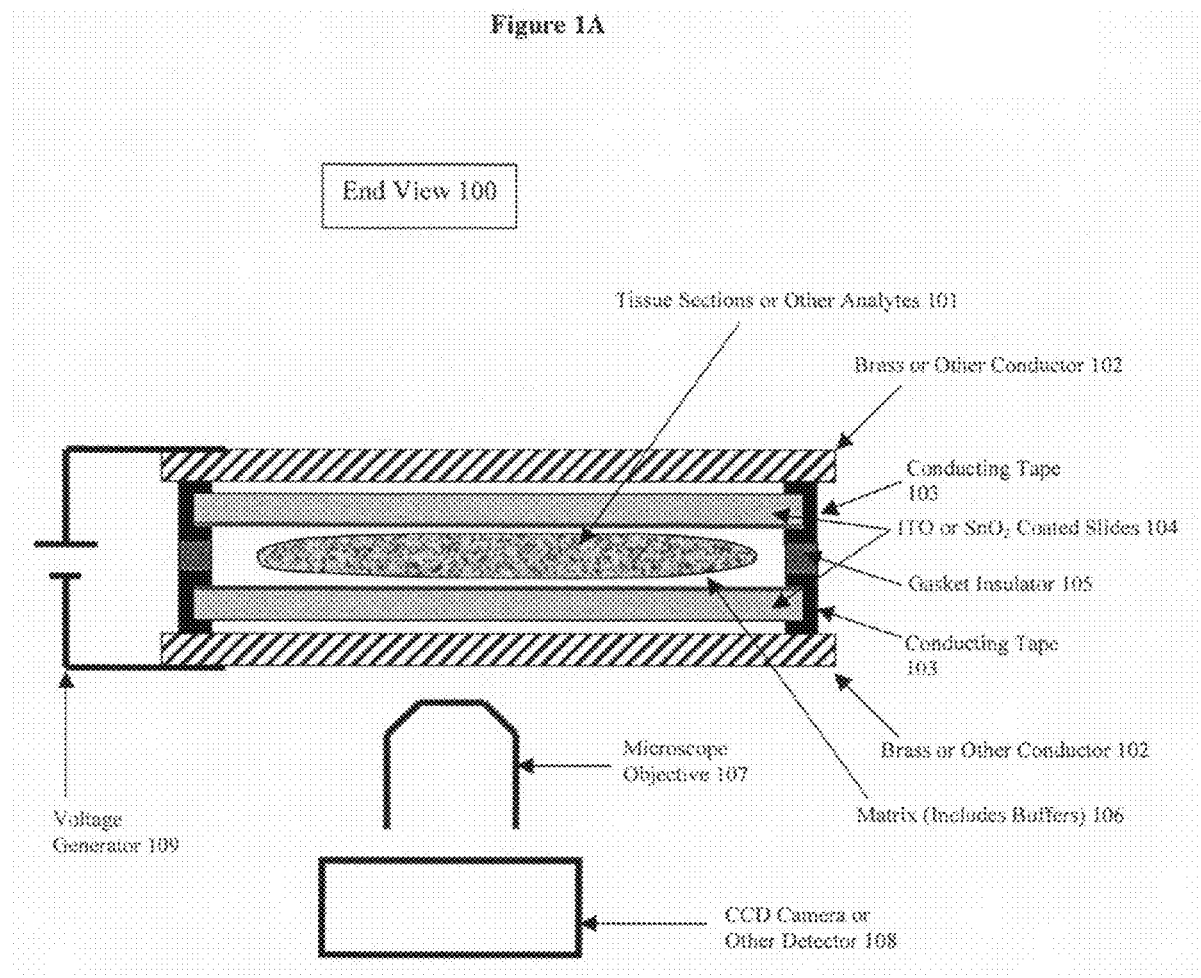

Figure 1B
Top View 100
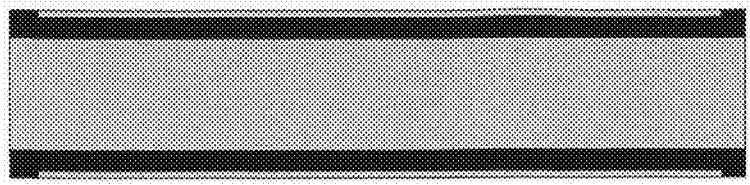
ITO or SnO₂ Coated Slide with Conducting Tape at Edges 104
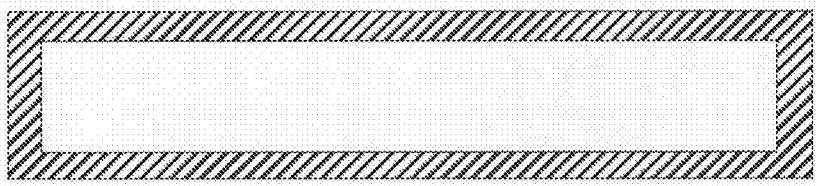
Brass or other Conductor 102
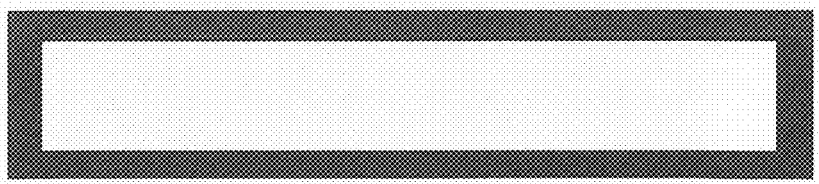
Gasket Insulator 105

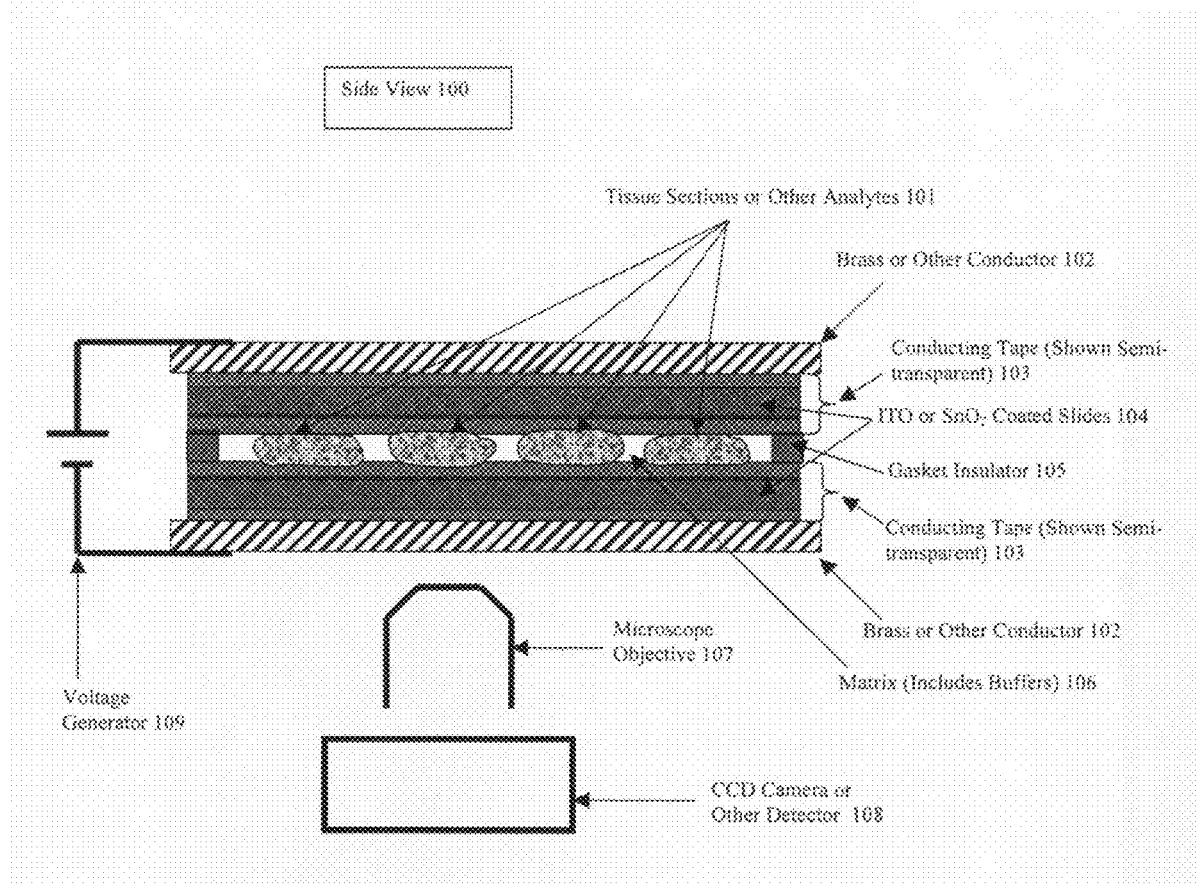

Figure 2

Molecular beacon for β-actin.

5' Rhodamine-red-CAC-CGC-TAG-ATG-GGC-ACA-GTG-TGG-GTG-ACG-CGG-TG-BlkHoleQ2-3'

|

Biotin

Figure 3

Steps in the preparation of biotin albumin coated sensor surfaces

1. Clean ITO slides in $H_2O/H_2O_2/NH_3$ (10:2:0.6) 55°C 75 minutes
2. Bake slides in vacuum oven 165°C 150 minutes
3. Cool with dry nitrogen and coat with SigmaCote
4. Coat slide with 0.05% bovine serum albumin-biotin (BSA-B) overnight
5. Wash in phosphate buffered saline (PBS) thoroughly
6. Coat BSA-B treated slide with streptavidin 0.1 mg/ml 60 minutes
7. Wash in PBS thoroughly
8. Coat streptavidin treated slide with molecular beacon (0.1 nMole/ml) 60 min
9. Wash thoroughly

Figure 4A

Routine suited for sensor in which molecular beacons are coated to the sensor surface throughout the analysis as in Example 1. Many other modifications of this will work also. Much higher frequencies would normally be employed (i.e., 200,000 Hz).

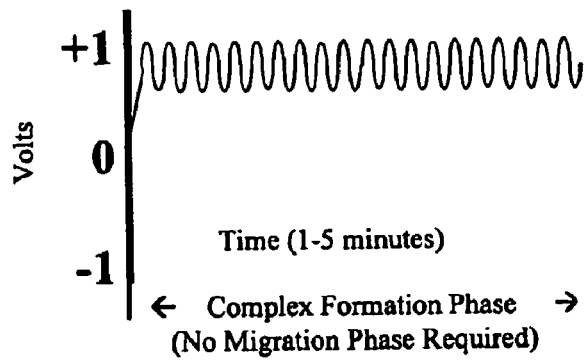

Figure 4B

Routine suited for sensor in which molecular beacons are not to the sensor surface and are free during analysis as in Example 2. Many other modifications of this will work also. Note the frequency shown is diagrammatic only. Much higher frequencies would normally be employed (i.e., 200,000 Hz).

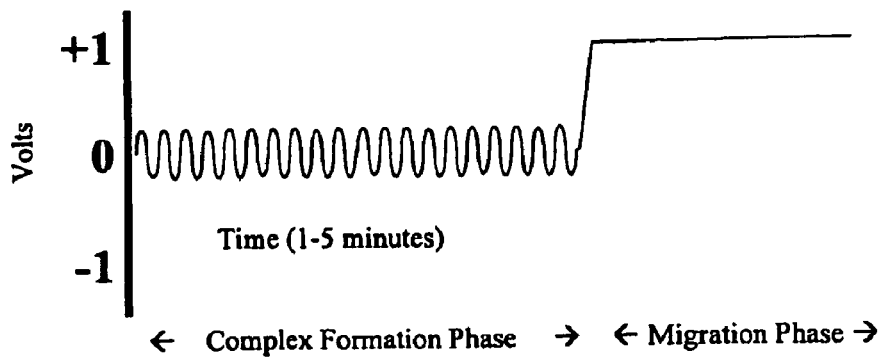

Step 1. Formation of the Complex (equal alternating potential)

ANODE / CATHODE            CATHODE / ANODE

Step 2. Migration of the complex to one electrode, away from the free fluorophore (potential is maintained)

ANODE                                CATHODE

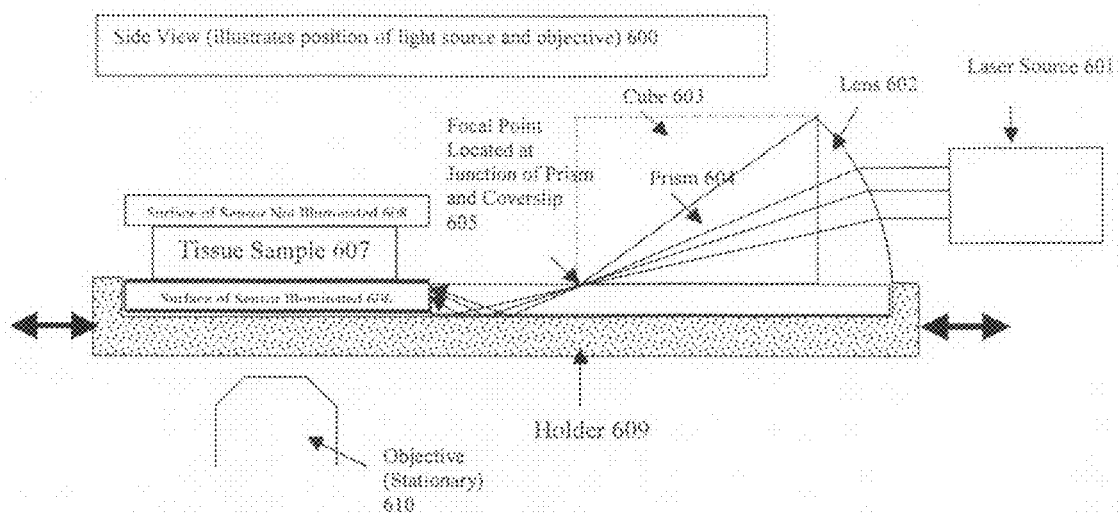
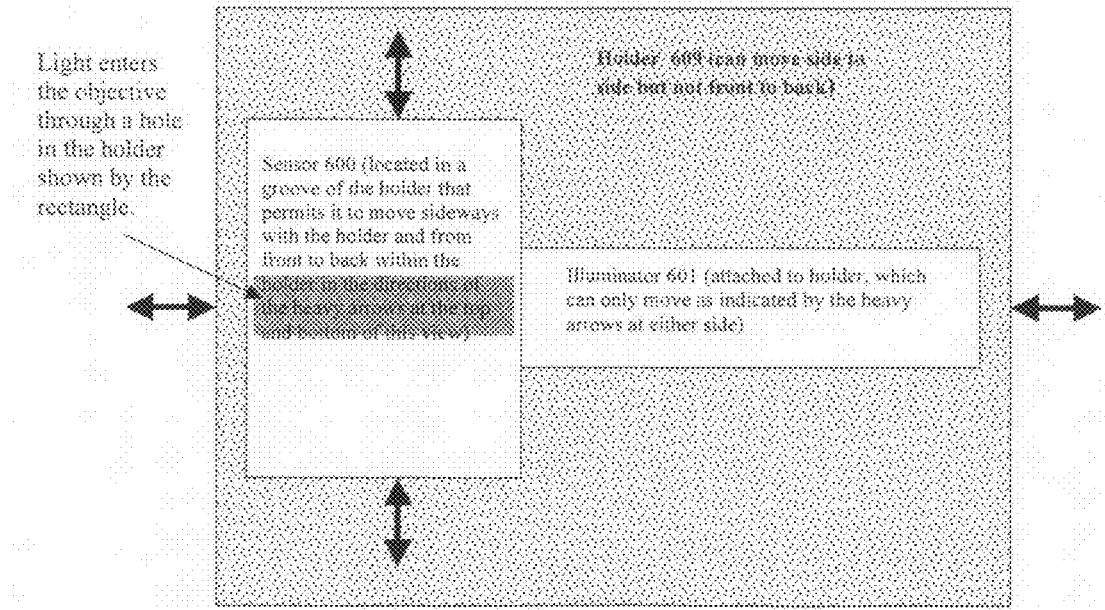

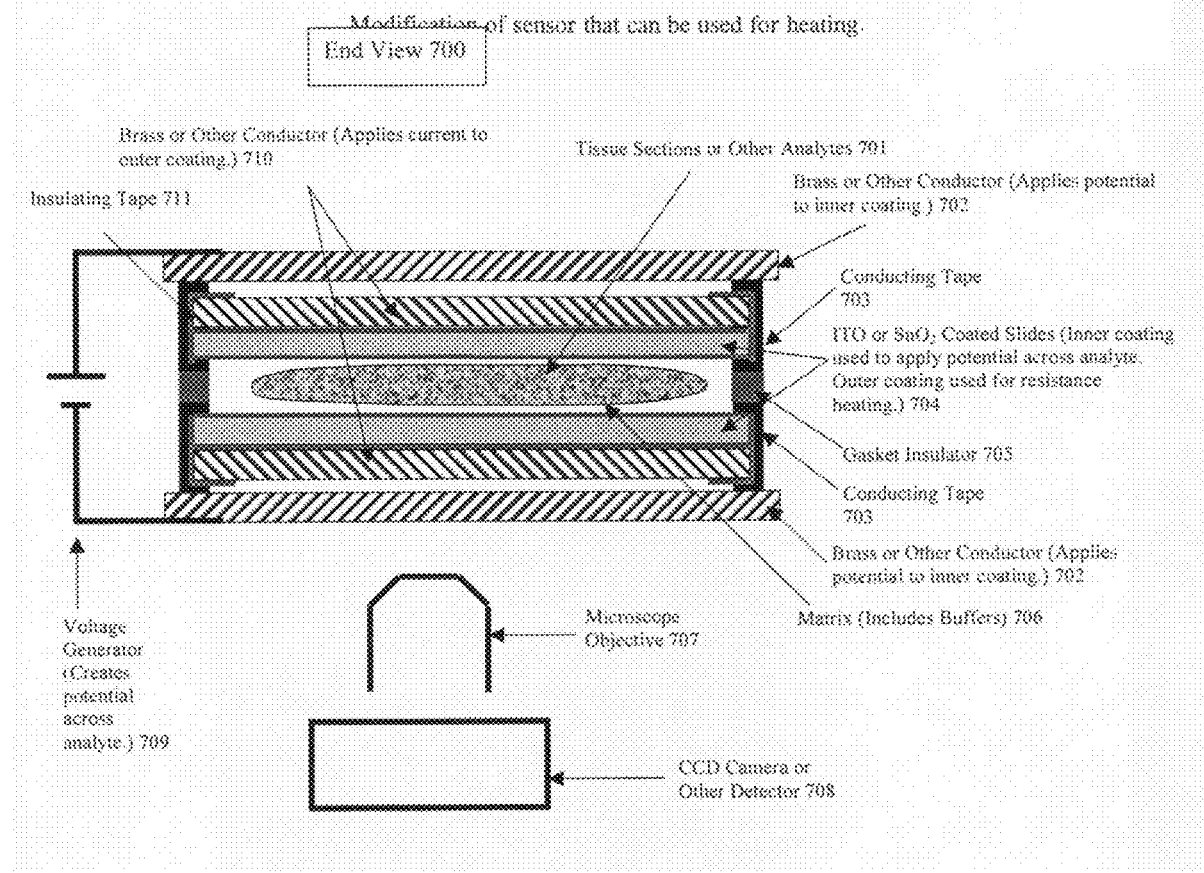

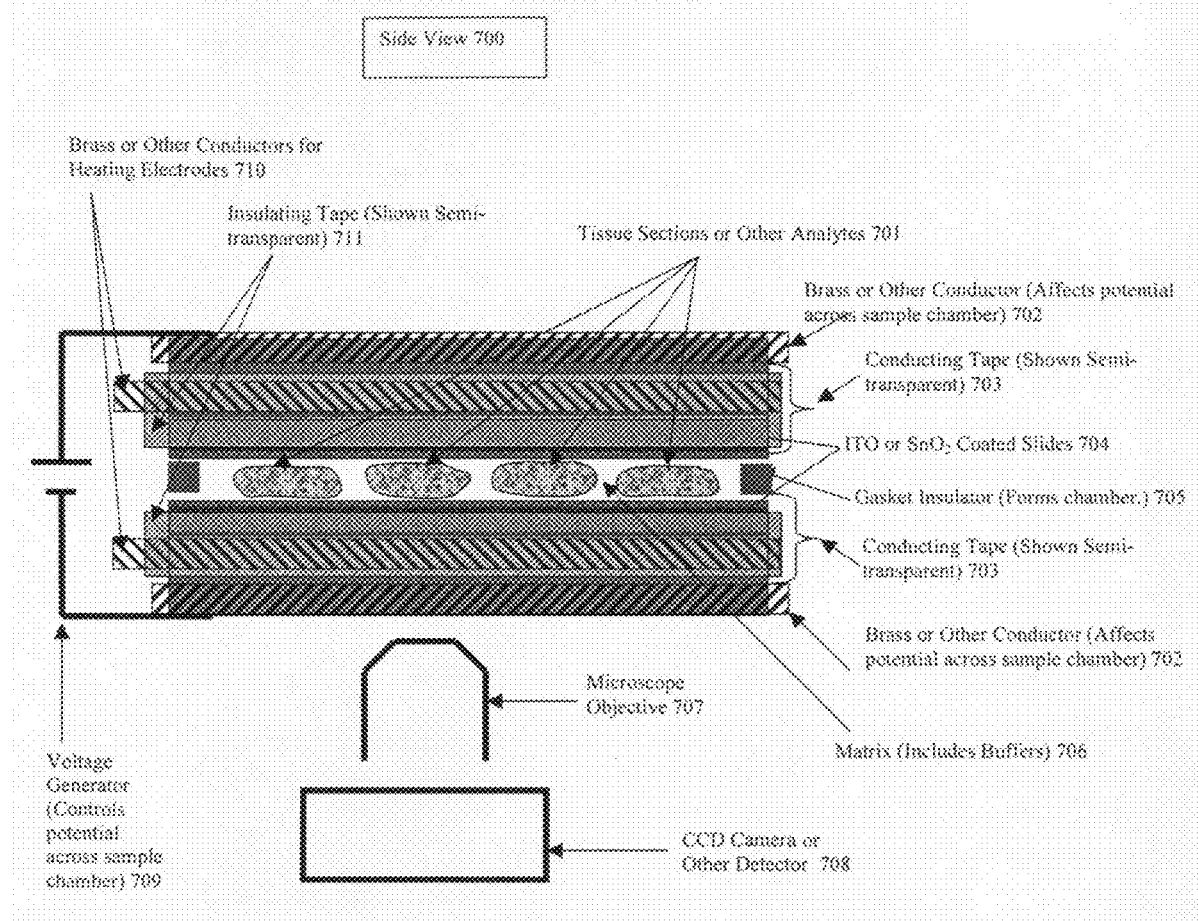

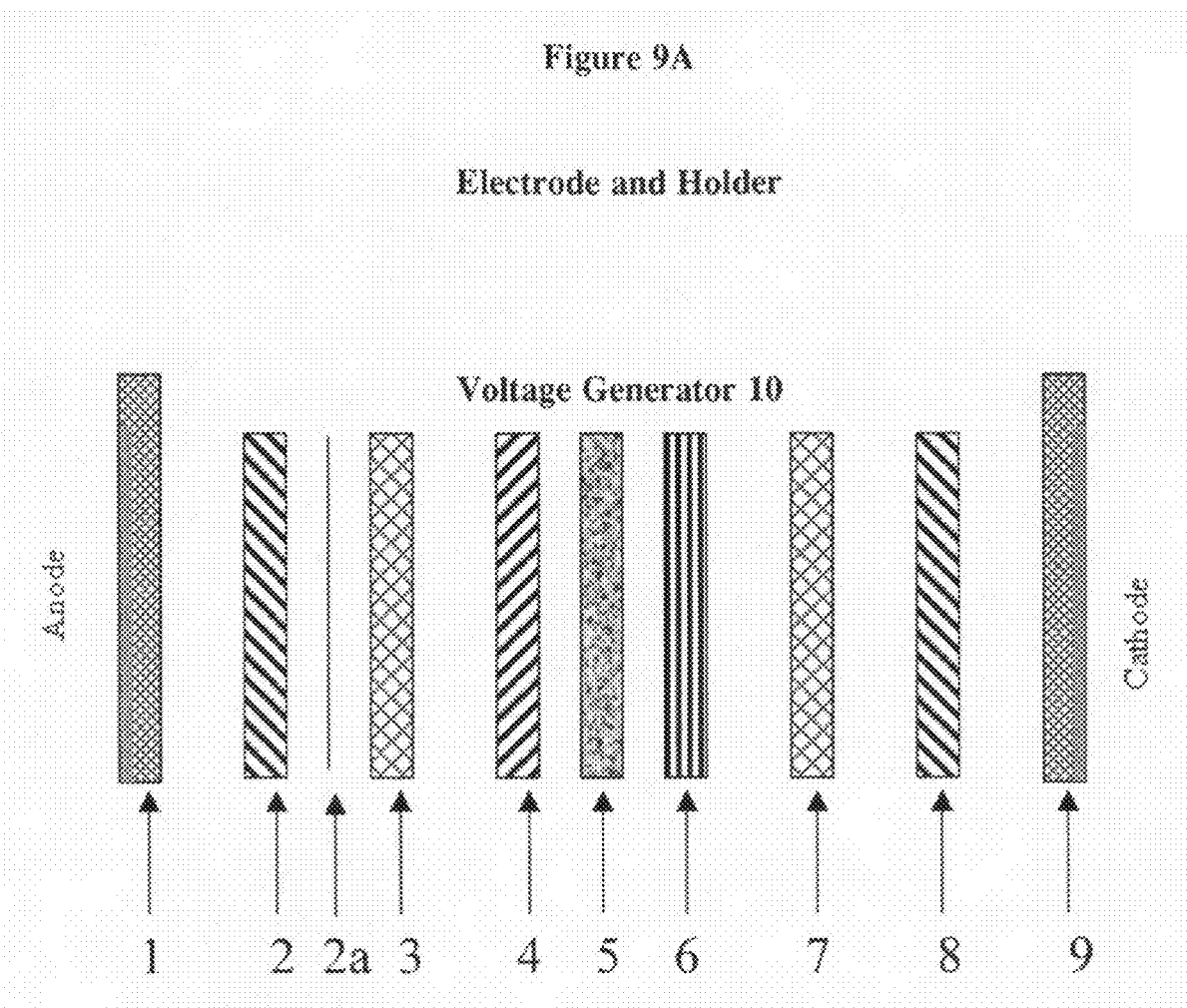

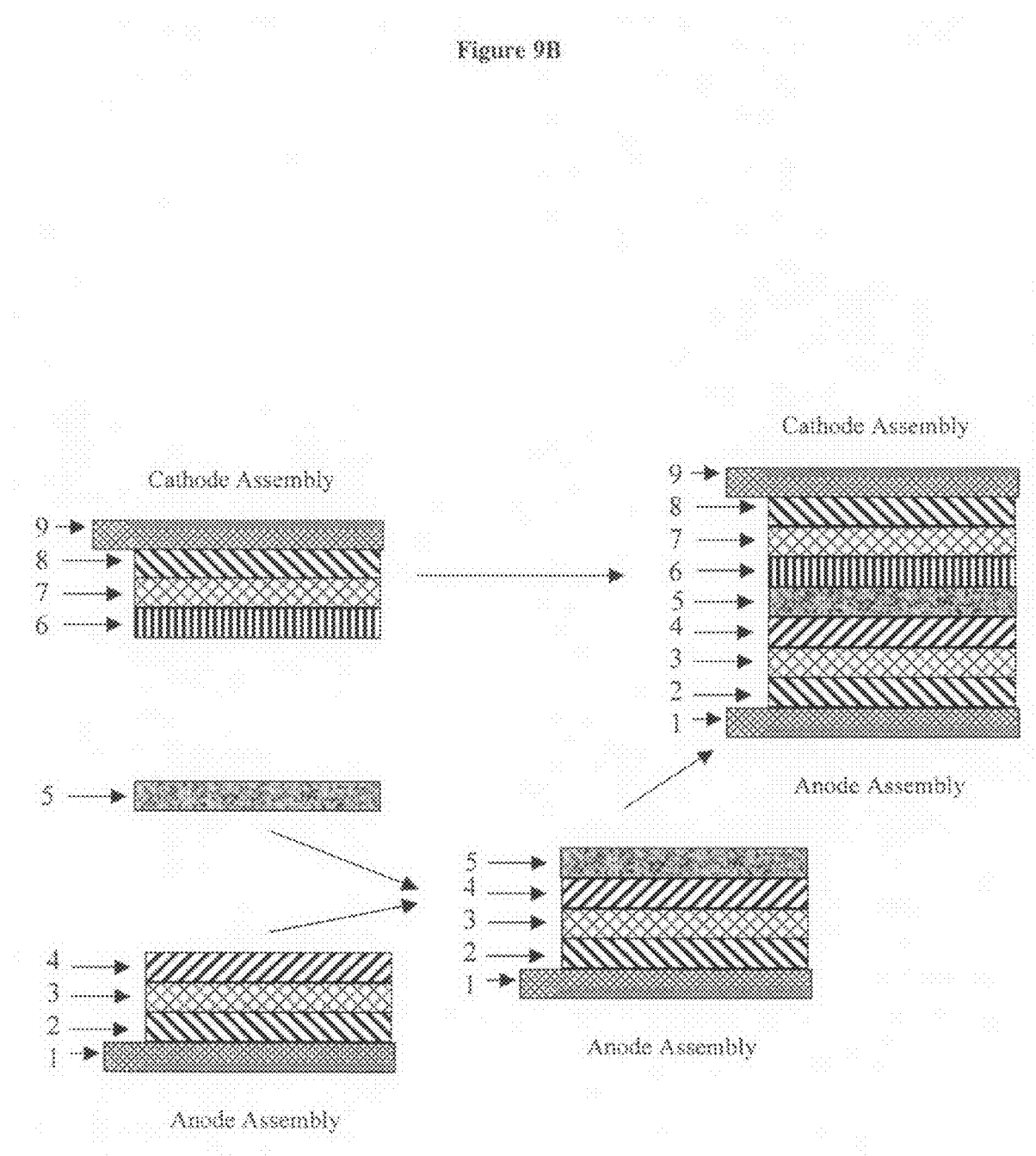

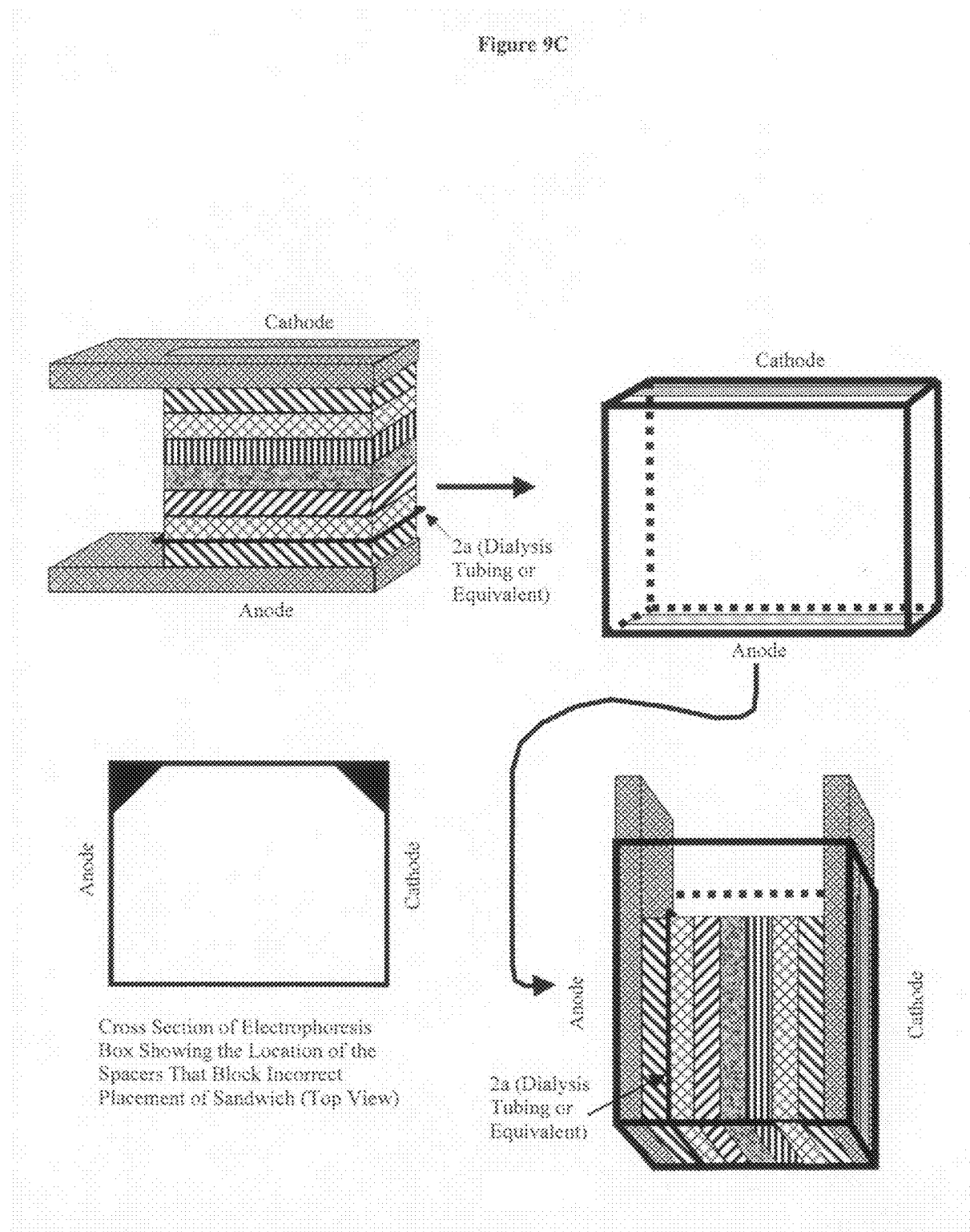

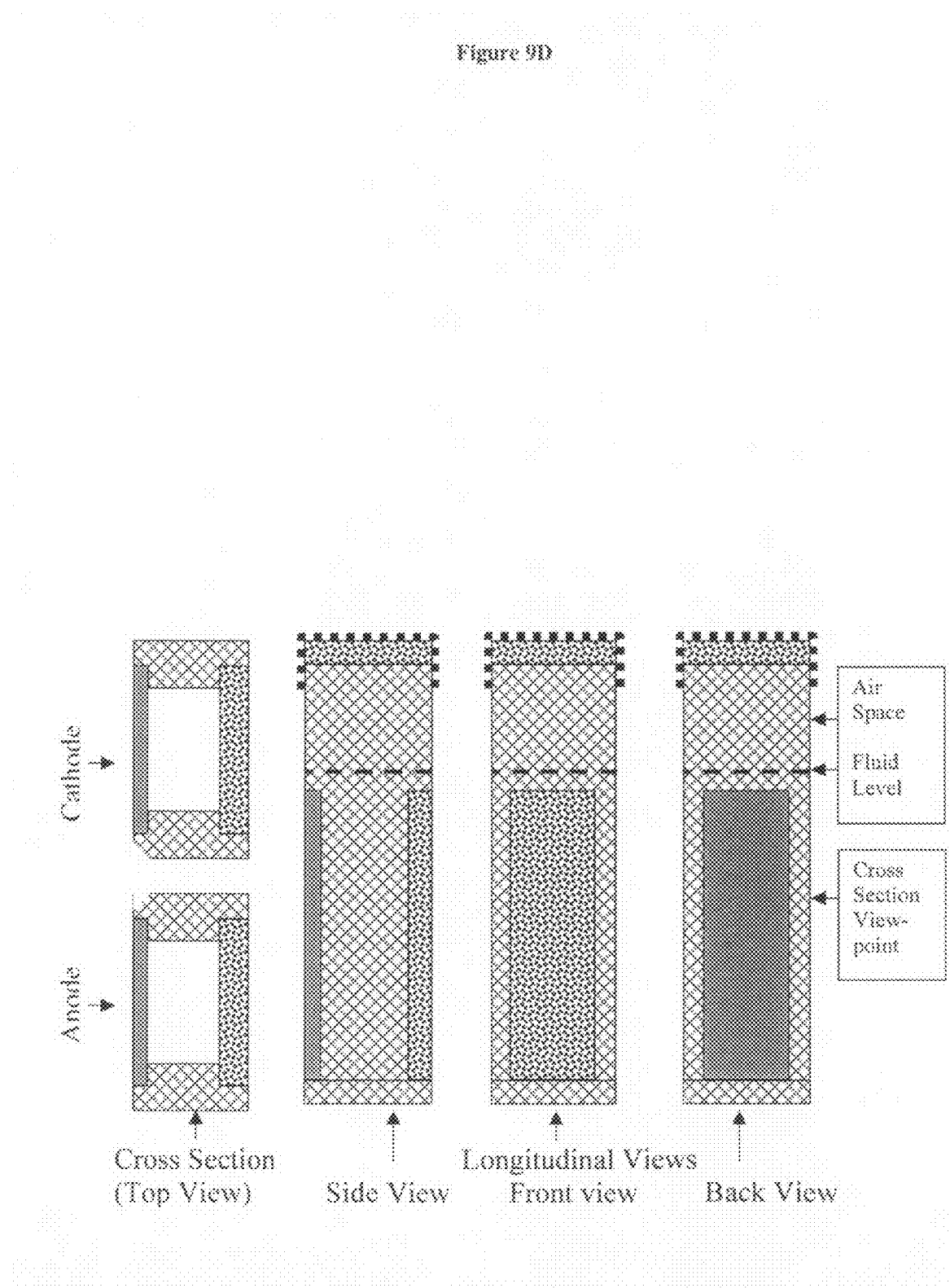

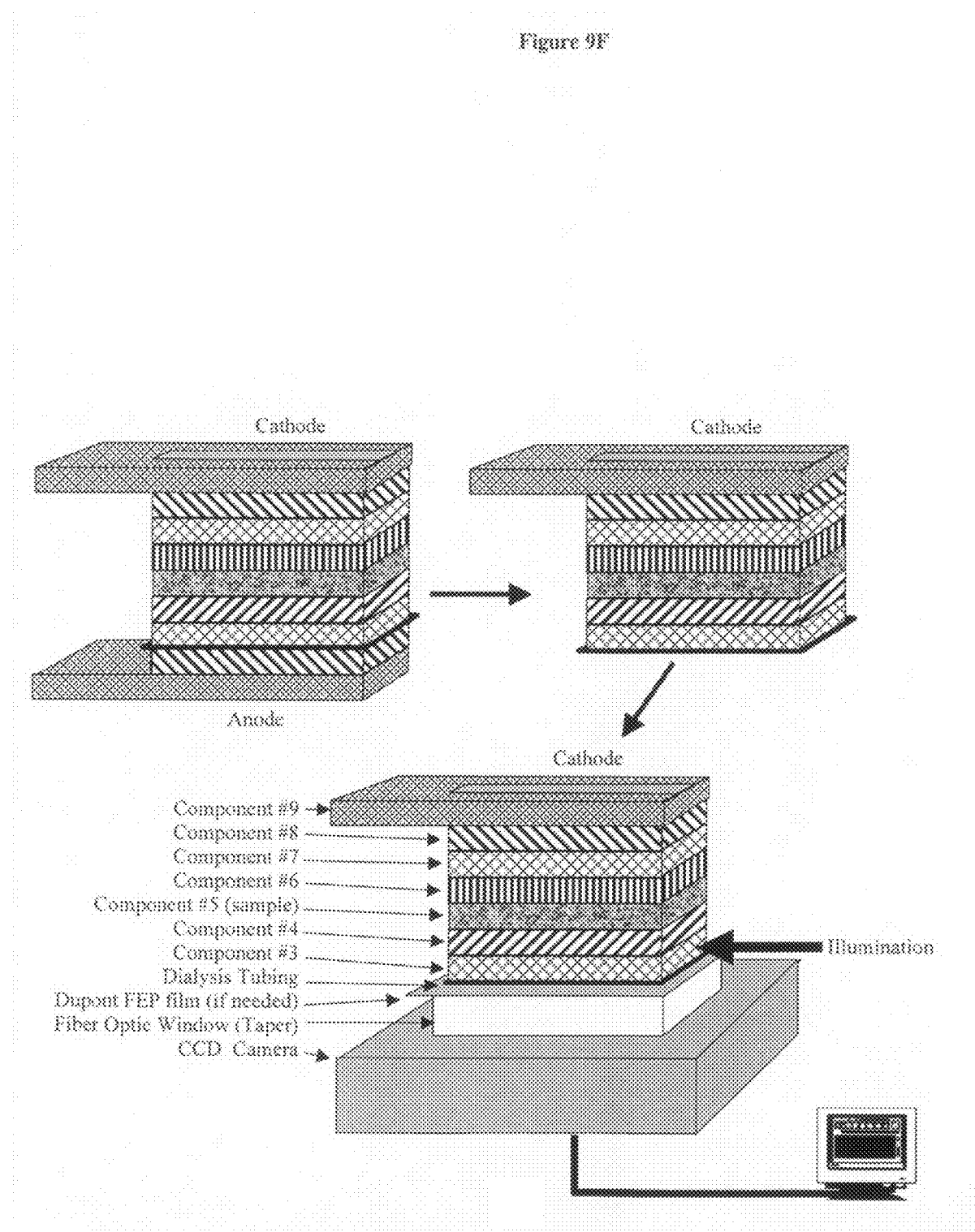

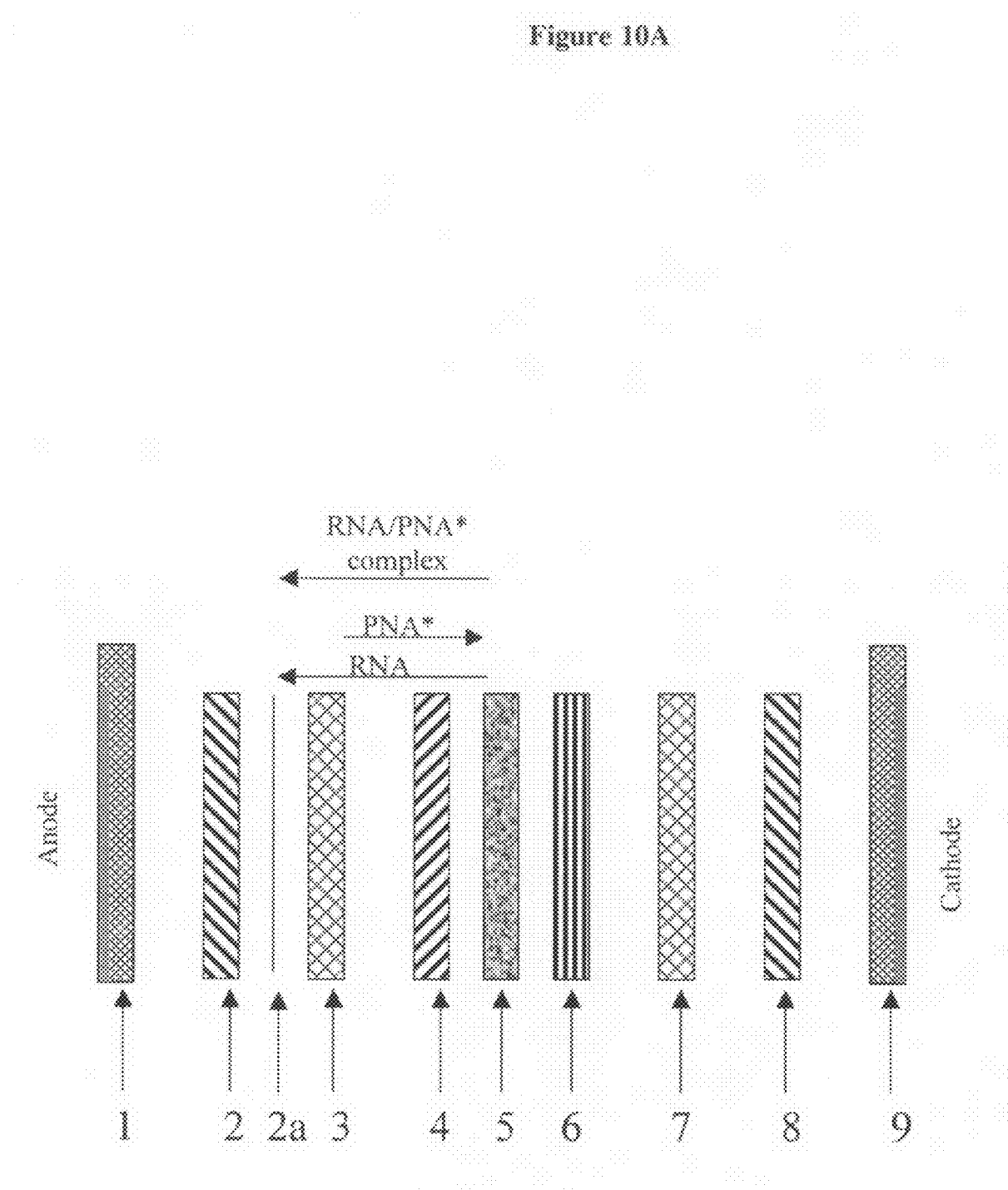

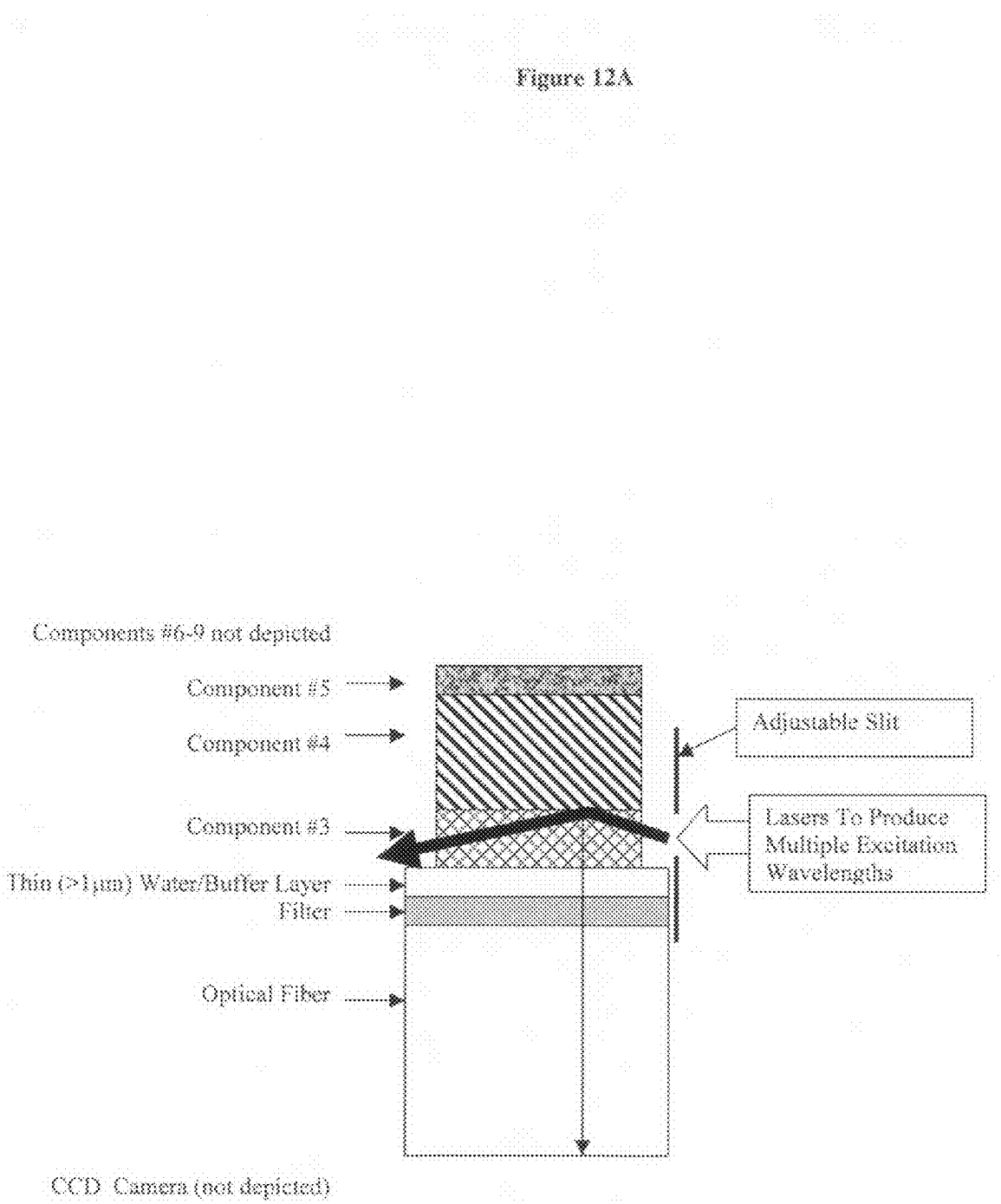

SENSORS FOR BIOMOLECULAR DETECTION AND CELL CLASSIFICATION

This application claims priority from PCT/US2003/031486, filed 3 Oct. 2003, which is a continuation-in-part application of PCT/US2003/13538, filed 30 Apr. 2003, which application was filed as U.S. patent Ser. No. 10/962,003 on 8 Oct. 2004.

BACKGROUND OF THE INVENTION

1. Field of the Invention

The invention relates generally to methods for detecting analytes such as proteins, peptides, nucleic acids, ligands, antigens, lipids, enzymes, and other molecules in simple and complex systems.

2. Description of the Background

The disclosures referred to herein to illustrate the background of the invention and to provide additional detail with respect to its practice are incorporated herein by reference and, for convenience, are numerically referenced in the following text and respectively grouped in the appended bibliography.

A device that can be used to monitor gene expression rapidly in single cells would have several important applications. For example, surgeons often rely on histological methods to distinguish tumor and normal tissues during surgery to remove cancers. These methods serve well when the morphology of the abnormal and normal cells is readily distinguished. Unfortunately, the borders of many tumors are not always well defined and do not provide clear landmarks that can be used to guide surgery. Further, it may be difficult to gauge the characteristics of the tumor even after sections have been stained with histological dyes. This can lead to unnecessary surgery during efforts to remove all the cancerous tissue. Indeed, some surgery for breast cancer involves removing lymph nodes to stage the cancer even though there often is no evidence that this additional surgery will be of significant benefit. Application of a technique that has the ability to monitor gene expression in these frozen sections would have considerable application during surgery to guide the procedure. It would also be useful to guide the type of therapy that is to be used following surgery.

Recent advances in genetics have provided the basis by which physicians and scientists have gained new insights into cell function. Bioinformatic analysis suggests that humans have 30-40 thousand genes [1;2] that are transcribed, spliced, and edited to yield 100 thousand mRNAs detected as expressed sequence tags [3]. This information has permitted the design of microarrays capable of monitoring thousands of gene products at one time [4;5]. Microarray technology is being applied widely to characterize changes in gene expression patterns that are associated with various tumors and with the prognosis of tumor therapy [5-7]. Indeed, there is considerable hope that the results of these studies will enable a more accurate classification of tumors and thereby guide the choice of therapy following surgery. One benefit of this may be a reduction in unnecessary chemotherapy or radiotherapy [5], procedures that often make patients ill and that may even be a source of malignancies later in life [8].

Further technical advances in measurements of gene expression products are required to take full advantage of the new information that is being made available from microarray measurements. Tumors are often quite complex and contain endothelial cells, fibroblasts, lymphocytes, and other cell types in addition to transformed cells. Microarray analyses of whole tumor tissues detect expression products of these cell types simultaneously [4;5], a phenomenon that confounds the association of particular gene expression patterns with specific tumor cells. These analyses can be further compromised by the presence of different types of tumor cells within the sample. Nonetheless, despite this complexity, gene expression patterns detected in some tumors are correlated highly with five-year survival rates [5] and this information can be used to facilitate tumor classification, the major parameter used to decide how patients are treated.

The massive amount of data obtained during microarray analysis is extremely valuable but it is confounded by the presence of gene products that have been obtained from multiple cell types. It can also be time-consuming to obtain and, because it contains so much information, can be difficult to interpret accurately. Results of array analyses indicate that it not necessary to monitor the expression of all possible genes to classify the tumor accurately [5;9]. In fact, as exemplified by findings made from studies of colon carcinomas, a majority of which have a preponderance of mutations of the APC and p53 genes [10], it appears that analysis of relatively few gene products would be adequate to classify tumors. The types of genes to be monitored can be determined by taking advantage of information that is usually known at the time of surgery, such as the location of the tumor (i.e., mammary gland, prostate, colon, lung, brain, etc.). The technology described here permits one to measure the expression of several gene products in single cells of frozen sections that are routinely prepared during surgical procedures. By focusing on genes whose expression has been found in microarray and other analyses to be most characteristic of a given tumor type, it will be possible to classify the tumor accurately. The devices taught here permit this information to be determined in a rapid fashion and can be used to form the basis of instant decisions needed for patient care.

The cells in a cancer have altered properties that enable them to evade apoptotic mechanisms that normally limit cell growth. Some of these include checks on the integrity of their genome and, when these are lost or become non-functional, cancer cells tend to accumulate mutations that make them more aggressive. Since not all the cells of a tumor have the same mutations, the tumor can be heterogeneous. The heterogeneity of some tumors may even be due to the fact that they have originated from several different cells, not just a single cell. Thus, to classify the tumor accurately, it is best to assess gene products from individual cells so that the degree of heterogeneity can be ascertained. It is also important to detect the existence and location of even a small number of cells that have reduced sensitivity to natural regulatory mechanisms. The ability to do so would enable pathologists and surgeons to learn if the tumor contains cells that have characteristics indicative of a more advanced stage of cancer as well as to learn where they are within the tumor. If this information were available at the time of surgery, it would enable the surgeon to tailor the surgical procedure appropriately for each patient. For example, the absence of these cells might indicate that it would not be essential to remove nearby or distant lymph nodes that are not part of the tumor. In contrast, the presence of a few advanced cells in a small otherwise unremarkable tumor might be grounds for more extensive surgery. Thus, it would be desirable to have a sensor that could quantify gene expression rapidly in single cells of frozen sections obtained at the time of surgery. Furthermore, this information should also affect the choice of post-surgical treatment such as chemotherapy and/or radiation therapy.

The therapeutic benefits of identifying cells that have altered genotypes and/or phenotypes that lead to pathological states have been recognized for many years. The need to classify these cells has led to developments of several methods for examining cells that range from simple staining procedures to highly refined approaches for identifying specific genes and gene products within the cell. Increased knowledge of cell function offers a greatly expanded number of markers that can be used to assess the pathological status of single cells.

Several methods have been developed to study gene function in individual cells. Fluorescence Activated Cell Sorting (FACS) methods have permitted individual cells to be isolated from complex cellular mixtures based on the use of antibodies to a single surface protein. This method requires disrupting tissues into their component cells, which is a time-consuming process that makes FACS analysis poorly suited for use as a routine surgical procedure. Techniques such as Fluorescent in situ Hybridization (FISH) are sufficient to detect single genes within cells of a tissue. The most sensitive of these techniques require considerable tissue preparation, however, and are not sufficiently rapid for routine use during surgery. Furthermore, the intrinsic fluorescence in cells and other factors often contribute to high background. This makes it essential to perform several time-consuming internal controls without which it would be impossible to interpret the analysis. Other properties of fluorescence, such as the ability of adjacent fluorophores to interact with one another, a process known as Fluorescent Resonant Energy Transfer (FRET), have been used to facilitate analyses of gene expression. For example it has been found that fluorescent oligonucleotides can be used to detect mRNA products of single genes cells based on the abilities of the oligonucleotides to bind to adjacent portions of the mRNA [11]. Nonetheless, these techniques can be plagued by the high intrinsic fluorescence of cells. While it is possible to circumvent this problem using time-resolved methods [12], this increases the complexity of the method substantially at the expense of assay sensitivity. In addition, there is a need to get the fluorophores into the cells where they can interact with the mRNA. Thus, this approach is not practical for routine examination of tissue sections. Efforts have also been made to monitor gene products using fiber optic techniques [13]. These methods are also not applicable to tissue sections and suffer from a very slow response time.

In summary, knowledge of the gene products that are associated with different pathologies is accumulating rapidly. The public availability of the sequence of the human genome and advances in microarray technology has permitted the simultaneous semi-quantitative measurements of large numbers of gene products. Array procedures have been used to characterize changes in gene expression in several types of normal and abnormal tissues. Indeed, comparisons of gene expression patterns in tumor tissues with tumor recurrence and long-term survival of patients following surgery, chemotherapy, and/or radiation have enabled predictions about the types of therapies that are most likely to be beneficial [4]. As noted earlier, array procedures are not readily adapted to analyses of single cells. Consequently, the data generated by application of this technique are confounded by the presence of analytes in non-tumor cells as well as by the fact that many tumors contain different types of abnormal cells. This makes it difficult to associate gene expression with particular cells in even a semi-quantitative fashion. Furthermore, array analysis is time-consuming and not suited for the rapid estimation of gene expression while the patient is in the operating room. Measurements of gene expression in single cells within the tumor would be of considerable value for classifying the tumor, a key component used to make informed decisions about the extent of surgery and subsequent therapies. It would also be applicable during research to learn which gene expression products are most likely to have predictive value. Finally, it would also be useful for studies of cell function during complex processes such as those that occur during development and cellular differentiation.

BRIEF DESCRIPTION OF THE FIGURES

FIGS. 1A-1C illustrate an overview of the sensor apparatus showing the sensor from three different perspectives. FIG. 1A shows an end view of the sensor.

FIG. 1B shows a top view of the sensor. FIG. 1C shows a side view of the sensor.

FIG. 2 shows the molecular beacon for β-actin (SEQ ID NO:1).

FIG. 3 shows the steps in the preparation of biotinylated sensor surfaces.

FIGS. 4A-4B illustrate the polarization routines. FIG. 4A shows negatively charged oligonucleotides migrating towards the positively charged sensor surface. FIG. 4B shows the use of a waveform to prevent premature separation of the analyte and the detection reagent (i.e., fluorescent PNA designed to contain a single positive charge).

FIG. 5A shows formation of the complex. FIG. 5B shows that during the separation phase, the fluorescent complex migrates to the anode where it would be observed and the fluorescent unbound PNA migrates to the cathode.

FIGS. 6A-6B illustrate TIRF illuminator for multiple objectives. FIG. 6A shows a side view with the position of the light source and objective. FIG. 6B illustrates the manner in which the illuminator would be mounted on a microscope.

FIGS. 7A-7B illustrate a modification of the sensor that can be used for heating. FIG. 7A is an end view of the sensor and FIG. 7B is a side view of the sensor.

FIGS. 9A-9F illustrate a polymer-based sensor device. FIG. 9A illustrates the overall design of the polymer-based device, which is shown in an expanded schematic form. FIG. 9B illustrates the device as it is being assembled. FIG. 9C illustrates the device as it is being used during electrophoresis. FIG. 9D illustrates the construction of the anode (component #1 plus component #2) and cathode (component #8 plus component #9). FIG. 9E illustrates the construction of the anode and cathode assemblies. FIG. 9F illustrates the mounting of the "exposed" sensor sandwich on the camera.

FIG. 10A-B illustrates the migration of PNA labeled with a fluorophore (PNA*). FIG. 10A illustrates the migration of PNA labeled with a fluorophore (PNA*) when it is free and bound to RNA in the sensor apparatus. FIG. 10B illustrates the migration of a fluorescent charged detection agent before and after its charges have been removed by an enzyme or a reaction with materials in or released from the tissue section.

FIG. 12A illustrates the arrangement of the system used to illuminate component #3 (or component #7, when used). FIG. 12B illustrates the illumination used to distinguish colors. FIG. 12C illustrates a preferred type of filter that can be used in the device to permit distinguishing colored fluorophores, if it is necessary to reduce the amount of scattered light. FIG. 12D illustrates a preferred mode for illuminating the sample.

SUMMARY OF THE INVENTION

Figure 5A:
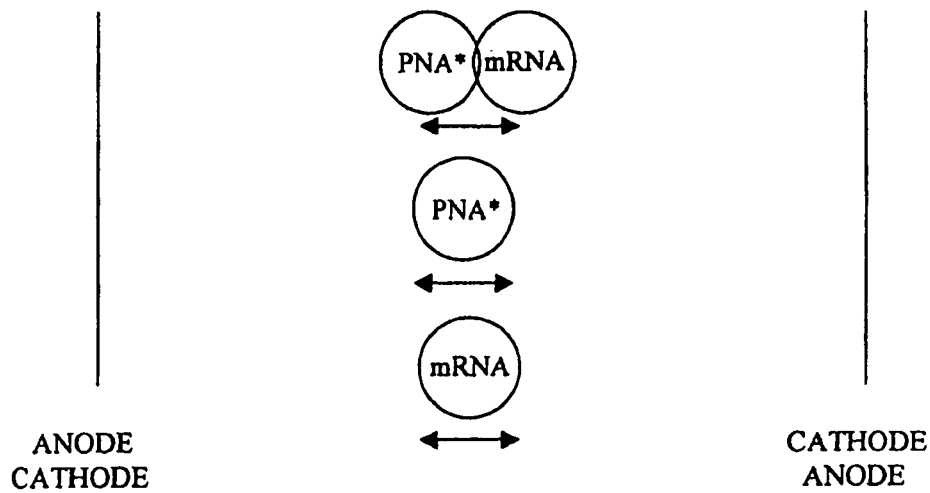
FIGS. 5A-5B illustrate the principle of sensor operation in Example 2.

The present invention provides a sensor device for detecting an analyte in a sample in which an analyte is bound to a detection reagent to form a bound complex, wherein the device comprises:

(a) a sample (5) comprising an ionic analyte and a detection reagent in a conductive fluid, wherein the detection reagent has a net charge different from the analyte;

(b) a first permeable polymeric hydrogel plate (3) and a first spacer plate (8), which plates provide a compartment for the sample;

(c) an anode (1) juxtaposed to the outside of the first hydrogel plate and not in contact with the sample;

(d) a cathode (9) juxtaposed to the outside of the first spacer plate and not in contact with the sample;

(e) a voltage generator (10) to apply an electric potential to the anode and cathode; and (f) a detector (11);

wherein the bound complex formed from the analyte and detection reagent is detected by the detector because the bound complex has a charge that causes it to migrate in a direction opposite from that of the unbound analyte when the electric potential is applied.

The present invention also provides a method for detecting an ionic analyte in a sample in which an analyte is bound to a detection reagent to form a bound complex, comprising the steps of:

(A) providing a sensor device comprising:

(a) a sample (5) comprising an ionic analyte and a detection reagent in a conductive fluid, wherein the detection reagent has a net charge different from the analyte;

(b) a first permeable polymeric hydrogel plate (3) and a first spacer plate (8), which plates provide a compartment for the sample;

(c) an anode (1) juxtaposed to the outside of the first hydrogel plate and not in contact with the sample;

(d) a cathode (9) juxtaposed to the outside of the first spacer plate and not in contact with the sample;

(e) a voltage generator (10) to apply an electric potential to the anode and cathode; and (f) a detector (11); and (B) adding the ionic analyte and detection reagent in the conductive fluid to the compartment;

(C) applying an electrical potential via the voltage generator; and (D) detecting via the detector the bound complex formed from the analyte because the bound complex has a charge that causes it to migrate in a direction opposite from that of the unbound analyte when the electric potential is applied.

The present invention also provides a sensor device for detecting and quantifying a gene product in a cell or tissue section sample by employing an analysis reagent that binds to the gene product to form a detectable product comprising:

(a) a first and second coated plate, wherein the plates are parallel to each other and are coated with a conductive material;

(b) a first and second conductive plate, wherein the plates are parallel to each other and are juxtaposed over the coated plates of (a);

(c) a first conducting tape connecting a first end of the coated plates of (a) and the conductive plates of (b) and a second conducting tape connecting a second end of the coated plates of (a) and the conductive plates of (b);

(d) a first gasket insulator insulating a first end of the coated plates of (a) and the conductive plates of (b) and a second gasket insulator insulating a second end of the coated plates of (a) and the conductive plates of (b);

(e) a voltage generator connected to the first and second conductive plates to apply an electric potential to the conductive plates; and (f) a detector;

wherein the first and second coated plates provide a compartment for a cell or tissue section sample and a conductive fluid and an analysis reagent is provided in the sample or tethered to a surface of the first or second coated plate such that when the voltage generator applies an electric potential to the conductive plates, the detector will detect the interaction between charged materials within the cell or tissue section sample, migrating towards either surface of the coated plate, and the analysis reagent.

The sensor device may further comprise a heating means to heat the sample prior to, or during, detection of the sample and may further comprise a cooling means to cool the sample prior to, or during, detection of the sample. The detector may be a fluorescence, luminescence, colorimetry, or total internal reflection illumination detector or may detect by phase contrast microscopy, bright field microscopy, darkfield microscopy, differential interference contrast microscopy, confocal microscopy, or epifluorescence microscopy. The electrical potential may be applied perpendicular to the coated plate and may be constant or varied such that the overall effect is to have each plate have a net charge, such that charged analytes in the tissues will migrate to one plate. The electrical potential may also be applied perpendicular to the coated plate and may be alternated such that there is no net charge on either plate, such that charged analytes will oscillate back and forth in the central space away from either plate where they interact with analysis reagents.

The present invention also provides a method for detecting and quantifying a gene product in a cell or tissue section sample by employing an analysis reagent that binds to the gene product to form a detectable product, wherein the analysis reagent is tethered to a surface of a sensor device, comprising the steps of:

(A) providing a sensor device comprising:

(a) a first and second coated plate, wherein the plates are parallel to each other and are coated with a conductive material, and an analysis reagent is tethered to a surface of the first or second coated plate;

(b) a first and second conductive plate, wherein the plates are parallel to each other and are juxtaposed over the coated plates of (a);

(c) a first conducting tape connecting a first end of the coated plates of (a) and the conductive plates of (b) and a second conducting tape connecting a second end of the coated plates of (a) and the conductive plates of (b);

(d) a first gasket insulator insulating a first end of the coated plates of (a) and the conductive plates of (b) and a second gasket insulator insulating a second end of the coated plates of (a) and the conductive plates of (b);

(e) a voltage generator connected to the first and second conductive plates to apply an electric potential to the conductive plates; and (f) a detector; and (B) adding a cell or tissue section sample and a conductive fluid to a compartment within the first and second coated plates of the sensor device;

(C) applying an electrical potential via the voltage generator to the conductive plates;

(D) detecting via the detector the interaction between charged materials within the cell or tissue section sample, migrating towards either surface of the coated plate, and the analysis reagent.

The present invention further provides a method for detecting and quantifying a gene product in a cell or tissue section sample by employing an analysis reagent that binds to the gene product to form a detectable product, wherein the analysis reagent is soluble in the sample, comprising the steps of:

(A) providing a sensor device comprising:

(a) a first and second coated plate, wherein the plates are parallel to each other and are coated with a conductive material;

(b) a first and second conductive plate, wherein the plates are parallel to each other and are juxtaposed over the coated plates of (a);

(c) a first conducting tape connecting a first end of the coated plates of (a) and the conductive plates of (b) and a second conducting tape connecting a second end of the coated plates of (a) and the conductive plates of (b);

(d) a first gasket insulator insulating a first end of the coated plates of (a) and the conductive plates of (b) and a second gasket insulator insulating a second end of the coated plates of (a) and the conductive plates of (b);

(e) a voltage generator connected to the first and second conductive plates to apply an electric potential to the conductive plates; and (f) a detector; and (B) adding a cell or tissue section sample, a conductive fluid, and a soluble analysis reagent to a compartment within the first and second coated plates of the sensor device;

(C) applying an electrical potential via the voltage generator to the conductive plates;

(D) detecting via the detector the interaction between charged materials within the cell or tissue section sample, migrating towards either surface of the coated plate, and the analysis reagent.

The detector may be a fluorescence, luminescence, colorimetry, or total internal reflection illumination detector or may detect by phase contrast microscopy, bright field microscopy, darkfield microscopy, differential interference contrast microscopy, confocal microscopy, or epifluorescence microscopy. The electrical potential may be applied perpendicular to the coated plate and may be constant or varied such that the overall effect is to have each plate have a net charge, such that charged analytes in the tissues will migrate to one plate. The electrical potential may also be applied perpendicular to the coated plate and may be alternated such that there is no net charge on either plate, such that charged analytes will oscillate back and forth in the central space away from either plate where they interact with analysis reagents. The gene products may be nucleic acids or proteins. The analysis reagent may be a biotin-streptavidin conjugate or may be a molecular beacon. Preferably, a mixture of molecular beacons labeled with the same fluorophore is employed to detect a mixture of gene products associated with a tumor class. A second molecular beacon may be employed as an internal control. Preferably, a first molecular beacon is employed to detect a control gene product and a second molecular beacon is employed to detect a gene product of experimental or diagnostic interest, wherein the first and second molecular beacons are each labeled with a different fluorophore that emits at a different wavelength so that the first and second molecular beacons can be simultaneously analyzed. The control gene product may be β-actin.

The transparent plates may be coated with indium tin oxide or tin dioxide.

DETAILED DESCRIPTION OF THE INVENTION

The present invention provides a rapid, sensitive, and accurate method that can be used to measure nearly any analyte. In particular, the method can be employed to visualize the relationship between gene expression and tissue morphology. The method utilizes an electrical potential to promote the movement of the analyte from one site to another causing the analyte to be concentrated in the region where the measurement can be made. By controlling the electrical potential it is possible to concentrate materials from tissue samples, electrophoresis gels, or any other media at a sensor surface and thereby enhance the sensitivity and the speed with which measurements can be made. Furthermore, the electrical potential can be used to reduce non-specific interactions that occur during analysis and thereby facilitate measurement accuracy. The electrical potential can also be used to alter the chemistry of the analyte and the sensor surface, and to immobilize sensor molecules at the surface via covalent bonds, coordination or physical adsorption. Analysis occurs by the specific interaction between the material that has migrated towards the surface of the plate and reagents that are attached to the plate or that are held near the plate surface. Because this analysis does not alter the relative positions of cells or other factors that are being analyzed, it permits the identification of analytes that are associated with specific cell types or with specific portions of the material being analyzed. The sample may also be reduced or oxidized to increase the specificity and accuracy of the device. The method permits decisions to be made by physicians and pathologists at the time of the procedure and facilitates analysis by persons less skilled in these tasks, such as technicians who do the preliminary reading of Pap tests and other analyses that are preformed in high volume on a routine basis. The information will also be useful for making decisions regarding treatments after the procedures are completed.

In one embodiment, the present invention can be used to measure gene expression products in tissue sections. These gene products can be nucleic acids, such as messenger and other RNAs, or proteins such as enzymes and transcription factors. The method proposed for use with tissue sections involves placing the tissue sections or cells, including those taken at time of surgery, between two transparent plates or slides that have been coated with a material that conducts electricity or that can be made to conduct electricity. When an electric potential is placed on either side of the tissue, charged materials within the tissue can be made to migrate towards either plate. Those with a net positive charge will migrate towards the cathode and those with a net negative charge will migrate towards the anode. The electrical potential on the transparent plates, which serve as electrodes, can be constant or varied in a variety of fashions. When the potential is constant or when it is varied such that the overall effect is to have each plate have a net charge, charged analytes in the tissues will migrate to one electrode. When the potential is alternated such that there is no net charge on either plate, charged analytes will oscillate back and forth in the central space away from either electrode where they interact with detection reagents.

The method is not limited to tissue sections but can be applied to detect other agents and may not require the use of two slides. Metabolites that are altered as the result of changes in gene expression may also be detected.

In a second embodiment, the sample is recognized by a binding agent in an interaction that occurs in solution and that can take place at either surface of the sensor device, in the vicinity of either surface, or away from either surface. The complex that is formed has a different electrical charge than the binding agent. Application of an electrical potential across the plates results in the migration of the complex towards one of the plates where it can be measured. Since the binding agent and the complex have different charges, it is possible to separate the binding agent from the complex, a phenomenon that can be employed to reduce measurement noise. When operated in this fashion, the device can be used to monitor any interaction that leads to a change in charge. This includes enzyme reactions in which enzymatic activity leads to a change in the charge of the substrate.

The actual measurement will be made when the charged materials reach the surfaces of one or both plates. In most cases, the measurement will depend on a change in fluorescence. There are two basic methods of examining fluorescence. In one method, a fluorophore will be attached to the surface. Migration of the analyte to the surface will cause an increase in fluorescence or a decrease in fluorescence of the bound detection reagent. For example, binding of the analyte to a molecular beacon would increase its fluorescence. While one could take advantage of a decrease in fluorescence caused by quenching, energy transfer, or even destruction of the surface fluorophore (e.g., by proteolysis or nuclease digestion), this would be less sensitive due to the fact that it would have a high background. The second method of detection depends on the ability of the analyte to cause the migration of a fluorophore to the surface. In this case, the fluorophore detection reagent is either uncharged or charged in a way that would cause it to migrate to the side of the device that is not being examined. Binding of the analyte to the fluorophore would change its net charge and cause it to migrate to the surface that is being examined. Since the charge on a fluorophore could also be changed by cutting the fluorophore or modifying it (i.e., adding a phosphate), this procedure would also permit detection of enzymes. This method could readily be used with quantum dots, fluorophores that are nearly indestructible and that are very bright.

Both methods have their advantages. The second method is preferable because it does not require surface labeling (a task that can require difficult chemistry), it enables the use of much higher reagent concentrations of reagents, and it can produce very low background because of the physical separation of the materials that occurs after electrophoresis. Advantages of the first method include the fact that the bound and free analytes are not separated, permitting detection of lower affinity interactions, and it can be used with a larger number of optical techniques. Indeed, since the fluorophore is attached to the surface, there is no need to use optical techniques that limit illumination to the surface.

The sensor device can also be heated and/or cooled to facilitate interactions between the reagents or even amplification of the analyte (i.e., by PCR). Fluorescence on the surface may be monitored using Total Internal Reflection Methods (TIRF), including TIRF microscopy (TIRFM) using methods that are well known in the art. A lens-based method has also been devised for extending these measurements. Another procedure for monitoring surface fluorescence involves the use of two photon methods. In these methods, photons that have insufficient energy to excite the sample individually are directed at the surface at the same time. When the photons reach the surface, the sum of their energies will excite the sample, enabling it to be detected. Another procedure that can be used is the employment of a lens that has a shallow depth of field that can be focused on the surface. Colorimetric methods can be also used, i.e., when the analyte-detection complex reaches the surface, it causes the appearance of a color.

When tissue sections are to be examined, it will be useful to have a method that can be used to scan the tissue sections automatically, freeing the surgeon or pathologist from spending time finding regions of greatest interest. Once these are detected by their fluorescence, they can be examined manually.

As set out above, detection of the interactions between the analytes and reagents may be carried out using fluorescence techniques although other visual methods including colorimetry and luminescence can be applied as well. One of the most useful techniques for detecting nucleic acid gene expression products such as mRNA employs molecular beacons. These can be attached to the surface of the sensor plate using a variety of methods. One of the most convenient involves attaching biotinylated molecular beacons to surfaces that have been coated with streptavidin. In this method, the beacon is synthesized as a biotin derivative by standard methods such as those employed by companies specializing in molecular beacon synthesis including IDT Technologies, Inc., Coralville, Iowa 52241, USA. Attachment of the biotinylated molecular beacon to the surface of the plate can be performed by attaching it to streptavidin that has been attached to the surface of the plate. Attachment of streptavidin to surfaces is well known in the art and can accomplished by reacting it with biotin derivatives that are covalently attached to the plate or by permitting it to interact with bovine serum albumin-biotin conjugates such as those obtained from Sigma Chemical Co., St. Louis, Mo. 63195, USA that have been adsorbed to the plate surface. Introduction of a charge between the plates of the sensor device promotes migration of the mRNA from the tissue to the positively charged surface of the sensor. This can be facilitated by the introduction of small quantities (i.e., 0.1-2%) of non-ionic detergents such as octylglucoside, which disrupt the plasma membranes that surround the cells in the tissue sections. It can also be facilitated by varying the charge on the plate surface in a fashion that prevents the negatively charged nucleic acid from sticking directly to the plate surface. Interaction of the mRNA gene products with the molecular beacon, a process that can be made to be highly specific by design of the molecular beacon using methods that are standard in the art will lead to increased fluorescence. Since this will be immediately above or below the material being analyzed, the amount of fluorescence will be roughly proportional to the amount of nucleic acid within cells or other local portions of the material being tested.

It is not necessary to use fluorescent reagents that are covalently attached to the surface of the sensor for analysis. For example, mRNA can be monitored using peptide nucleic acids (PNA), which are analogs of nucleic acids that have the sugar-phosphate backbone replaced by peptide bonds. PNA have the same binding specificity as nucleic acids and can be designed using the same principles as are well known in the art to construct oligonucleotides that interact with nucleic acids. PNA are superior to nucleic acids for measurement in the sensor, however, because they lack the strong negatively charged phosphate backbone structures characteristic of nucleic acids. Thus, PNA are essentially neutral in physiological buffers and do not have a great propensity to migrate to either surface of the measuring device. When they bind to mRNA or other nucleic acids, the complex becomes negatively charged due to the negatively charged backbones of the part of the complex derived from the nucleic acid. Thus, the complex will migrate towards an anode. If the PNA are made to contain a fluorophore, formation of the complex will cause the fluorophore to migrate towards the anode where it can be readily detected using TIRFM, confocal microscopy, microscopic techniques that employ two or three photons to excite the sample, or by use of an objective that has a very shallow depth of field. If the fluorophore that is attached to the PNA is positively charged, unbound PNA molecules will migrate towards the cathode. Thus, by measuring fluorescence at the anode, it is possible to detect and quantify specific mRNA gene products in samples.

While nearly any procedure capable of detecting fluorescence can be used to detect the material, it is often most useful to perform the technique in an optical microscope. In cases where the background fluorescence that may be present in tissues and tissue sections is found to limit the sensitivity of the technique, one can also apply microscopic techniques such as TIRFM a device that is constructed specifically for this purpose and that is readily adapted to routine use. TIRFM is a very sensitive procedure that permits studies of single molecules and has even been used to investigate the folding of single molecules of RNA [14]. TIRFM takes advantage of a physical characteristic of electromagnetic radiation that occurs when light reflects from the interface between two optical media that differ in refractive index. In TIRFM a beam of light is passed through a material of high refractive index (e.g., glass, fused silica, sapphire) such that it reaches an interface with a material of lower refractive index (e.g. aqueous solution, tissue section). When the angle of incidence is below a value known as the critical angle, all the light is reflected back into the material of high refractive index. A standing electromagnetic or "evanescent" wave will be generated at the interface. Its energy will be maximal at the interface and will decay exponentially as a function of distance from the surface of higher refractive index, e.g., as the electromagnetic wave penetrates into an aqueous medium. The energy in the evanescent wave light can excite fluorophores that are attached to the surface or that are in close proximity (100-400 nm) to the surface of high refractive index. The limited distance traveled by the evanescent wave is responsible for the ability of TIRFM to illuminate material that is on or very near the surface of the TIRFM sensor (i.e., the material of high refractive index). As a consequence of the physical principle that underlies TIRFM, the unwanted background light that results from the intrinsic fluorescence of tissue samples that is often a problem for other types of fluorescent microscopy is virtually eliminated. This high signal-to-noise ratio is responsible for the ability of TIRFM to detect and quantify trace amounts of material in the face of an overwhelming amount of non-specific contaminating debris.

Use of TIRFM can also permit use of the sensor for analysis under conditions in which the reagents that are being used to detect the analyte are not necessarily attached to the sensor surface. Thus, when fluorescent PNA are added to the tissue sections that have been treated with agents such as non-ionic detergents that disrupt the integrity of the cell membrane but not the overall architecture of the tissue, they will interact with nucleic acid gene products (i.e., mRNA and other RNA polymerase derived nucleic acids). Application of an electric potential will cause the fluorescent PNA-RNA hybrid complexes to migrate to the sensor surface where they can be detected. Since multiple PNA can be employed and since multiple fluorophores can be employed, this technique permits simultaneous measurement of many different analytes, a significant advantage during studies to identify gene expression products.

Addition of an electrochemical polarization to the sensor surface used in TIRFM can increase the sensitivity and the speed of analysis further. Coating of the TIRFM sensor chip with a thin layer of indium tin oxide (ITO), tin dioxide ($SnO_2$), or several other metals does not affect its ability to be used for TIRFM at near ultraviolet or visible light wavelengths. Application of an electrical potential to the metal coating can be used to enhance the concentration of material at the sensor surface. This can increase the sensitivity of detection as well as the speed with which the measurements can be made. For example, by varying the electrical field on the TIRFM sensor surface, it is possible to facilitate the migration of nucleic acid oligomers to the surface of the sensor where they can hybridize with others that are on the sensor surface. The presence of an electric field can also facilitate the release of mRNA from tissue sections by disrupting the plasma membranes, a process known as electroporation. This will enhance the migration of mRNA towards the anode sensor surface. It will also facilitate interactions of mRNA with other agents such as PNA. When appropriate fluorophores such as molecular beacons are attached to the sensor surface, it is possible to use this principle to selectively measure nearly any gene product in single cells. Since tissue sections are applied directly on the sensor surface during surgery, this procedure results in a rapid and quantitative analysis of gene products within cells and will permit distinguishing the expression patterns cells within the tissue.

Several different types of fluorophores have been incorporated into molecules than can be used for detection and companies such as Molecular Probes, Eugene, Oreg. and Integrated DNA Technologies (IDT), Coralville, Iowa market them. One of the most useful properties of fluorophores is their ability to undergo resonance energy transfer (RET), also known as fluorescent resonance energy transfer (FRET). RET between adjacent fluorophores occurs when the adsorption spectrum of one overlaps the fluorescence spectrum of the other. According to principles first established by Förster [15], the amount of RET between two fluorophores varies as the inverse of the distance between them to the sixth power. Thus, RET will be nearly quantitative when the fluorophores are adjacent and virtually undetectable when the fluorophores are separated by as little as 100 Å and, in many cases, even less. During RET, energy from the fluorophore that adsorbs light at shorter wavelengths is transferred to that of the fluorophore whose adsorption spectrum overlaps the emission spectrum of the first fluorophore. This leads to a reduction in the amount of light emitted from the first fluorophore and an increase in the amount of light emitted from the second fluorophore. The reduction of light emitted by the first fluorophore can be used to estimate the distance between the fluorophores. It can also be used to assess the formation of a complex between two molecules that are labeled with fluorophores that are capable of undergoing RET. RET between two fluorophores usually leads to a change in the spectrum of light that is emitted. Measurements of the emission spectrum are also useful for quantifying the distance between the two fluorophores and have been widely used to monitor enzyme reactions, such as that seen in the presence of β-lactamase. RET is also useful for quantifying analytes as well as interactions between ligands and receptors. Its uses for these purposes are well known.

Not all molecules that adsorb light fluoresce. When RET occurs between a fluorophore and non-fluorescent molecule, the latter will quench the fluorescence of the fluorophore. When the fluorophore and the quenching molecule are sufficiently close to one another, all or nearly all the fluorescent energy will be quenched and little or no light will be emitted.

This property is particularly useful for detecting analytes that disrupt contacts between the fluorophore and the quenching molecule since the amount of light that is emitted will be directly proportional to the amount of the analyte. In the absence of analyte, none of the light will be emitted, resulting in a very low assay blank. This property led to the development of "molecular beacons" [16], hairpin shaped molecules designed for the measurement of nucleic acids. In the absence of analyte, the end of the molecular beacon that contains the fluorophore is held adjacent to the end of the molecular beacon that contains the quenching molecule by hydrogen bonds similar to those responsible for the hybridization of nucleic acids. When these interactions are disrupted by the binding of a second molecule of nucleic acid, the distance between the fluorophore and the quenching molecule exceeds that needed for RET and the fluorescence becomes readily visible. By combining RET and TIRFM, it is possible to enhance the desirable properties associated with each technology, thereby facilitating the measurements of analytes. The combined sensitivity of RET and TIRFM has permitted studies of single molecules [14].

In a preferred application of the device, the application of an electric field causes the analyte to migrate to the sensor surface where it interacts with an immobilized molecular beacon or other fluorophore. This results in a change in fluorescence of the immobilized fluorophore. Molecular beacons are particularly well suited for use in this device since their fluorescence increases upon interaction with nucleic acids in a highly sensitive and predictable fashion. One of the limitations of this type of sensor is the need to attach the agent to the sensor surface. This requires additional steps in sensor construction and can be limited by the amount of material that can be attached to the surface. While these limitations are usually not severe, they can increase the costs of sensor construction. A wide range of chemistries is available for attaching materials to the surface of sensors used in the device and reagents for doing so are available from several companies including United Chemical Technologies, Inc., 2731 Bartram Road, Bristol Pa. 19007. Furthermore, it is possible to increase the "depth" of the surface considerably by attaching compounds such as dextran that can serve as additional attachment points.

It is not necessary to attach the detection reagent to the surface to operate the device, however, and another preferred embodiment of the sensor is based on the use of soluble detection reagents. These can have considerable advantages to the use of surface bound material. First, since soluble reagents are not coupled to the sensor surface, their use facilitates sensor design by eliminating the surface-coupling step. Second, they can often be used in massive excess, a phenomenon that can increase the sensitivity and speed of detection. Third, they can be designed in a manner that prevents them from reaching the surface unless they have interacted with the analyte. This can reduce the background fluorescence observed in the absence of analyte. Indeed, the excess reagent can be designed such that it will migrate away from the sensor surface during analysis, a phenomenon that can minimize the background further. Fourth, interaction of the detection reagents and the analyte can take place away from the surface, which minimizes artifacts caused by surface phenomena. These include non-specific adsorption to the surface, which can prevent interactions between the analyte and the detection reagent. While these can also be minimized by varying the potential on the surface of the device, this adds an additional complication to the analytical procedure. Fifth, these reagents are readily adapted to use with quantum nanodots, fluorophores that are not readily photobleached and that have a very high quantum efficiency. Quantum nanodots can be purchased from the Quantum Dot Corporation, 26118 Research Road, Hayward Calif. 94545, USA. Furthermore, quantum nanodots can be excited at short wavelengths and have narrow fluorescence spectra. This permits the simultaneous detection of multiple analytes following excitation with only a single laser beam, a major advantage in analysis of gene expression where it is desirable to observe many gene products at one time.

The need for analytes to reach the sensor surface before they can be observed, a property of TIRFM that facilitates distinguishing specific from non-specific interactions, can result in slow response times. This can also reduce the sensitivity of TIRFM, particularly if the substance to be measured is prevented from reaching the sensor surface. Gene expression products such as mRNA or proteins that are held in tissue sections would not be expected to section such that charged analytes are driven to the surface of the sensor where they can be detected. The application of a charge perpendicular to the tissue section also reduces lateral diffusion of the gene products thereby increasing the likelihood that the fluorescence observed is associated with the cell that is expressing the gene. In addition, by varying the charge, it is possible to accelerate interactions between surface molecules and to reduce non-specific binding.

TIRF can also be monitored without the use of a high-magnification microscope lens. In this case one loses the spatial resolution needed to identify individual cells within a sample. Nonetheless, there are times when it useful to monitor light emission over a large areas, such as during efforts to scan the perimeter of a tumor to determine if the edges have been removed during surgery. There are few limits to the size of the TIRF sensor and it is envisioned that sensors of sizes other than those used commonly by pathologists will be of value for the technique.

Measurements of TIRFM can be done at several different magnifications through the use of an objective prism. High magnification TIRFM using commercially available 60× and 100× microscope objectives can currently be accomplished using devices that have been specifically designed for this purpose. Useful equipment for this purpose can be purchased from Nikon microscope dealers such as Micron Optics, 240 Cedar Knolls Road, Cedar Knolls, N.J. 07927 USA. In these devices, a laser beam is directed through the objective, an oil layer, and a thin coverslip of approximately 0.17 mm. These devices are excellent for visualizing fluorescence in tissue samples. When used with differential interference optics (DIC), these microscopes can also be used to monitor the cells from which the analytes are derived.

Due to the high power of the objective lenses that are used in the commercial microscopes for TIRFM, it is difficult to scan tissue sections in a rapid fashion. There is a need for lower power TIRFM that can also be used with the sensor. As taught here, this is met by designing a new method for illuminating the samples. The use of this strategy to monitor a broad image permits much more rapid scanning of the sample.

Data collection can be made using a charge coupled device (CCD) camera or related cameras of sufficient sensitivity, many of which are available commercially and are available from microscope dealers such as Micron Optics. Intensified CCD cameras are also available that are much more sensitive. These can also be purchased from most microscope dealers. Measurement of light intensity can also be done using photomultipliers that are attached to one of the optical ports on most high quality microscopes. One useful instrument that has been designed for this purpose can be purchased from C&L Instruments, 314 Scout Lane, Hummelstown, Pa. 17036 USA.

Even with the use of low power objectives, it is often desirable to scan the surface of the sensor. This permits one to detect gene products in subsets of tissue sections and thereby distinguish normal and pathological tissues. This process can be accomplished manually by moving the microscope stage that holds the sensor. It can also be accomplished automatically using computer driven stages that are available from most microscope dealers. By combining the use of computer driven stage movements and data collection, it is possible to devise an image of the entire sensor surface at high resolution. The operator can then examine those regions of particular interest, a time saving feature of the method.

The analytical techniques taught here are not restricted to the analysis of nucleic acids, although this will be an important use. For example it is possible to measure proteases by permitting them to cleave specific substrates that are attached to the sensor surface. One such method involves the preparation of peptides that contain a fluorophore and a quencher. Proteolysis of the peptide liberates the fluorophore from the quencher, resulting in enhanced fluorescence. Proteolysis can also remove charged components of the substrate that permits it and its attached fluorophore to migrate to the sensor surface for observation. Similarly, the technique can be applied to the measurements of kinases and phosphatases, enzymes that alter the phosphorylation status and hence the charge of an analyte. Changes in the charges of fluorescent kinase and phosphatase substrates can be used to promote migration of the substrates to a sensor surface where they can be measured. This forms the basis for the enzymatic analyses of these agents as well.

It is not essential to use fluorescent techniques for detection of the analytes that are to be measured. Enzymatic analytes can be often be detected by virtue of their enzymatic activity which can lead to the deposition of colored reagents on the surface of the sensor.

As setout above, the present method can also be used to measure changes in the charge of any fluorescent material caused by interaction with an analyte, including a binding molecule or an enzyme. It can also be caused by a cascade of events such as multiple enzyme-coupled reactions.

The present invention is further illustrated by the following examples, which are not intended to limit the effective scope of the claims. All parts and percentages in the examples and throughout the specification and claims are by weight of the final composition unless otherwise specified.

EXAMPLES

Example 1

A Sensor Device to Monitor Gene Expression in Frozen Tissue Sections in which the Analysis Reagents are Tethered to One Surface of the Device During the Entire Analytical Procedure FIG. 1 illustrates the features of a sensor device that will enable the measurement of gene products in cells of tissue sections. This preferred embodiment of the device consists of two plates placed on opposite sides of the material to be analyzed (i.e., the tissue sections). While it would be possible to detect some gene products by pressing the plates against the tissue sections, this is relatively inefficient process and is difficult to control adequately. A preferable mode of operation is to introduce an electrical field between the plates perpendicular to the tissue as shown in FIG. 1. The potential used can be varied within wide limits but should usually be less than that which promotes the electrolysis of water to prevent the accumulation of gas bubbles in the device. Thus, for frozen tissue sections that are roughly 200 µm thick, this will result in an electrical potential of 50 volts per cm more or less, a value that is much greater than the amount needed to promote rapid electrophoresis of nucleic acids such as mRNA. The electrophoretic mobility of the mRNA in tissue samples can be impeded by the cell membranes, however, even when the tissues are partially damaged by freezing and thawing during tissue sectioning. Gene products can usually be made more available for analysis by the inclusion of agents such as non-ionic detergents (e.g., 0.1-1% octylglucoside) or other agents that disrupt cell membranes without drastically altering the cytoskeletal and other structural components of the cell. Disruption of the tissue can be minimized by using the smallest amounts of these agents possible. Care should be taken to reduce tissue damage when histological analysis of the tissue sections is to be compared with the results of gene expression analysis.

There are two principle methods that can be used to detect negatively charged RNA polymerase generated gene products using the device illustrated in FIG. 1. In one, the detection reagent (e.g., a molecular beacon) is attached to the surface of the plate that will serve as the anode. In the other, which will be described in Example 2, the detection reagent becomes located near the anode during the procedure.

Attachment of detection reagents to the sensor surface can be done by a variety of methods. One of the most convenient is to use a biotin-streptavidin conjugation procedure. In this method a biotin moiety is attached to the surface directly by chemically attaching a biotin derivative to a properly derivatized surface or indirectly by adsorbing a bovine serum albumin biotin complex to the sensor surface. The biotinylated surface is then reacted with streptavidin, a protein that contains four biotin binding sites. Binding of streptavidin to the surface creates a biotin binding site on the surface, which can be used to immobilize biotinylated detection reagents such as biotinylated molecular beacons. Incorporation of biotin into the beacons can be done at the time they are synthesized. For example the beacon illustrated in FIG. 2, which was designed to recognize β-actin, contains a biotin that was incorporated during its synthesis by IDT DNA Technologies, Inc. This was done to permit its attachment to streptavidin that was purchased from Sigma, St. Louis, Mo., 63178, which had been attached to biotinylated-bovine serum albumin (also purchased from Sigma) that had been adsorbed to the surface of indium tin oxide (ITO) coated slides purchased from Delta Technologies. USA (FIG. 3).

Many methods for preparation of chemically biotinylated ITO surfaces are well known in the art. One method that is useful involves cleaning ITO coated slides by treating them with $H_2O/H_2O_2/NH_3$ in a ratio of 10:2:0.6 at 55° C. for 75 minutes followed by baking them in a vacuum oven at 165° C. for 150 minutes to remove water. The slides are then cooled in dry nitrogen and treated with 0.5% 3-aminopropyltrimethoxysilane in toluene. Both reagents can be obtained from Sigma-Aldrich, St. Louis, Mo. They are then washed with methanol and the resulting surface amino groups are biotinylated by reacting the slides with a biotin analog that is reactive with amino groups such as biotinamidocaproate, N-hydroxysuccinimidyl ester obtained from Molecular Probes, 29851 Willow Creek Road, Eugene, Oreg. 97402.

The chemically cleaned slides can also be treated with other agents that permit them to be derivatized with thiol, aldehyde, and other groups that facilitate conjugation with biotin containing and other compounds. They can also be treated with agents that cause them to be derivatized with polyethylene glycol (PEG) and PEG derivatives that can be purchased from Shearwater Corp. (U.S.), 1112 Church Str., Huntsville, Ala. 35801. They can also be treated with reagents such as Sigmacote obtained from Sigma, that renders the surface hydrophobic and that facilitates the adsorption of biotinylated serum albumin.

Introduction of an electrical potential across the ITO or other metal coated slides used to fabricate the optically transparent chamber walls will cause negatively charged gene products such as mRNA to migrate towards the anode where they can interact with detection reagents such as molecular beacons. Indeed, molecular beacons are preferred detection reagents since they usually have low background fluorescence in the absence of analyte and can be designed to interact specifically with predetermined gene products using methods well known in the art. Indeed, companies that specialize in the synthesis of DNA and molecular beacons such as IDT DNA Technologies, Inc. offer a service in which they assist in the design of properly functioning beacons.

The molecular beacon will become much more fluorescent when it binds the analyte for which it has been designed, a phenomenon that causes the shape of the beacon to be altered and that displaces the quenching agent from the fluorophore. For the mRNA to interact with the beacon, it must travel from the cellular milieu to the anode sensor surface. This is facilitated by the presence of the electric potential. Interaction of the mRNA with the molecular beacon can be enhanced by varying the potential used to cause migration of the gene product to the anode. A diagram representing a typical polarization pattern that can improve the interaction of the mRNA and the beacon is illustrated in FIG. 4. Many variations on this theme will give adequate mRNA beacon interactions that are useful for measurement of gene expression, however, and it is not essential to use that illustrated here. Variation in the potential can be performed with a potentiostat or similar device. Useful instruments include that from CH Instruments, 3700 Tennison Hill Drive, Austin, Tex. 78733, USA.

While a single molecular beacon can be used during analysis, it is usually preferable to employ at least two different beacons, one of which is intended to serve as an internal methodological control. This beacon can be made to detect gene products such as β-actin that are found in abundant amounts in most cells and whose expression is not changed significantly during most pathologies. The other beacon can be made to detect products that are of experimental or diagnostic interest and should be labeled with a fluorophore that emits at a different wavelength to permit its simultaneous analysis with the control beacon. The finding that the ratios of these gene products change provides strong indication that significant changes in gene expression have occurred within the tissue. Furthermore, many tissue sections will contain more than one cell type. Another control would be to compare the expression of actin in each cell type with the expression of the gene product that is associated with a pathological condition.

The choice of the gene products to be measured for experimental or diagnostic purposes will depend on the results of preliminary studies or of published microarray analyses, many of which are already known to those familiar with the art. Furthermore, it may be desirable to monitor multiple gene products of diagnostic interest at the same time. For example, as noted earlier, microarray analysis has indicated that several different gene products are associated with specific types of breast carcinomas. By using mixtures of beacons that are labeled with the same fluorophore and that recognize several gene products associated with tumor class one can increase the chances of detecting this type of tumor. This is because the interaction of any or all of these gene products with these beacons will be associated with a particular fluorescent emission spectrum. By labeling pools of beacons that recognize gene products associated with a different type of tumor with a fluorophore that has a different emission spectrum, it is possible to detect and classify pathological cells derived from more than one class within the tumor or to more accurately classify the tumor type, a significant advance in diagnostic practice. Since analysis can be done on sections obtained at the time of surgery, use of the sensor makes it possible for the surgeon and pathologist to modify the surgical procedure in the most appropriate fashion for the patient during the procedure.

There are two principle advantages that accrue from operating the sensor using detection reagents that are attached to its surface. The first is simplicity of analysis. Since the detection reagents are physically separated from the tissues throughout the procedure, it is not necessary to use methods that limit fluorescence excitation to the anode or cathode. Thus, while procedures such as TIRFM and multiple photon excitation can be used to monitor interactions between the beacons and the gene products on one sensor surface, the fact that the beacons are found only on this surface means that these techniques are not required. Indeed, it is often possible to use standard fluorescence microscope techniques when the background illumination can be adequately controlled. This reduces the costs of the instrumentation required. And second, use of surface bound fluorophores does not require physical separation of bound and non-bound analytes. This permits monitoring of low affinity interactions. While this is not a problem with the molecular beacons, it can be an issue for other types of analytical procedures such as interactions between fluorophores and surface bound proteins.

The advantages of using immobilized detection reagents can be offset by several factors including difficulties in attaching them to the surface, limits to the amount of material that can be attached to the surface, effects on ligand recognition caused by their attachment to the sensor surface, the need to employ organic dyes that can photobleach, and the influence of non-specific interactions. The latter can often be minimized by the use of agents such as bovine serum albumin and polyethylene glycol to block these interactions. The limitation on the number of groups that can be placed on the sensor surface can be offset in part by increasing the surface area by coating it with dextran and other agents that serve as attachment sites. These techniques are all well known to those familiar with the art.

Example 2

A Sensor Device to Monitor Gene Expression in Frozen Tissue Sections in which the Analysis Reagents Move with the Gene Products to the Anode During Analysis The second preferred embodiment, the device shown in FIG. 1, employs detection reagents that are not attached stably to either sensor surface. Analysis depends on the migration of the detection reagent to either the cathode or anode following interaction with the analyte. This approach circumvents many of the limitations that result from using surface immobilized detection reagents. Detection occurs when the complex reaches the one or other surface, depending on its charge.

Figure 5:

A diagram outlining the mechanism by which this sensor operates is shown in FIG. 5. Basically, the agents that interact with the analyte are either uncharged or weakly charged such that they tend to migrate to the surface of the device opposite that being used to sense the analyte. mRNA gene products can be measured in this device using PNA (peptide nucleic acids), which are similar to ribonucleic acids except that the ribose-phosphate backbone is replaced by a peptide bond. This makes them uncharged but does not affect their abilities to form heterodimers with complementary RNA sequences. These can be attached to fluorophores and it would be expected that they can also be attached to quantum nanodots. The latter reagents would have significant advantages due to their resistance to photobleaching and their high intrinsic fluorescence. Binding of mRNA to the fluorescent PNA molecules causes them to become negatively charged, a phenomenon that causes them to migrate to the anode sensor surface where they can be detected by their fluorescence.

There are several advantages to detecting analytes using soluble reagents that can be separated in an electric field. First, there is no need to attach them covalently to the sensor surface. This simplifies the design of the device. Second the fluorophores migrate to the sensor surface only when they have formed a complex with the analyte, a phenomenon that provides an intrinsic mechanism to limit background fluorescence. In fact, since the PNA-fluorophore complex can be made to have a weak positive charge, molecules that are not bound to the mRNA gene products will migrate away from the sensor surface. As a result, a massive reagent excess can be used within the device without causing an unacceptable increase in background noise. The fact that a larger amount of these reagents can be used in the device also increases its sensitivity and the speed with which it can be operated. Finally, as will be noted in later examples, the mechanism that underlies this analytical approach can be used to monitor gene products other than nucleic acids.

These advantages of using soluble reagents for analysis of nucleotide based gene products are offset in part by the requirement that illumination be limited to the anode sensor surface. One practical approach for doing this is to use devices that illuminate the surface by total internal reflection. This limits illumination to the surface of the sensor used for detection. Equipment for TIRFM is commercially available from microscope dealers who handle instruments made by either Nikon or Olympus. Instruments purchased from these companies are limited to relatively high power objectives, however (i.e., 60× and 100×). This can make it difficult to scan rapidly an entire sensor surface. There are other strategies for performing TIRFM that can be used with lower power objectives. These involve illuminating the sample through a prism such as that shown in FIG. 6.

Another means of illuminating the anode surface is to use two or three photon microscopy or confocal microscopy. In the former approach, the anode surface would be illuminated such that that single photons are unable to excite the sample. Focusing the illumination source on the sensor surface to cause it to be illuminated "simultaneously" by two or more photons provides sufficient energy to obtain fluorescence emission. The major limitation to the routine use of this type of illumination is its high cost.

Separation of the bound and free detection reagents is done by application of the electric field, which causes the bound detection reagent to migrate to the anode when the complex is negatively charged or to the cathode when the complex is positively charged. The rate at which the analyte will reach the surface will depend on the difference in potential between the plates, the frequency with which the potential on the plates is changed, the size and charge of the analyte, and factors that may limit its ability to migrate to the surface of the plate. Variations in the electric field can be very useful for causing the complex to form. Thus, by alternating the electric field, one can cause charged analytes to migrate back and forth within the region of the sensors. This creates a mixing effect that can enhance interactions between the analytes and the detection reagents that facilitate formation of the complexes.

Example 3

Details of Sensor Construction

The sensor described in FIG. 1 contains two glass, quartz, sapphire, mica, plastic, or other plates that are optically transparent at the illumination and fluorescent wavelengths to be used. This permits direct visualization of fluorescence or other optical events that result from interactions of the analyte with materials in the sensor. It is often convenient to use standard microscope slides or coverslips for construction of the optical portions of the sensor and it is not necessary that both slides be made of the same material. In fact, unless the sensor is to be used for visual observation of its contents, it is not necessary that both surfaces of the sensor be constructed of optically transparent materials. Indeed, it is possible to remove one surface of the sensor prior to examining its contents.

The sensor surfaces are coated with ITO, $SnO_2$, or other conducting or semi-conducting materials that are also optically transparent at the wavelengths to be used. This is done to enable an electric potential to be developed between these two surfaces. While this is a preferable means of designing the electrical components of the sensor since it permits both the optical and electrical components to be combined, workable sensors can be envisioned that would contain conducting grids or membranes in place of one or both of these surfaces.

The device outlined in FIG. 1 contains a second metal coated surface that is transparent to light. It is not essential that this surface be transparent to light unless one wants observe the tissue sections by phase contrast or other regular light microscopic techniques without removing it. In some cases, it may be desirable to remove the surface prior to observation by regular light microscopy since this will permit the tissue to be stained using a histological dye before or after the analysis by TIRFM. It is also not essential to use a solid surface as the electrode. For example it is possible to use a metal screen, metal grid, wire, semitransparent metal coating, or any other device that can be used to apply a voltage across the tissue section.

Several methods can be used to deliver an electrical potential to the surface of the plates. In one procedure, the entire plate is coated with ITO or other conducting metal. When this is placed on a metal wire or other conducting surface, it will permit the introduction of an electrical potential on all portions of the plate, including that in contact with the sample. Another method of connecting the conducting surface of the plate to the wire or conducting surface must be used when only one surface of the plate that contacts the sample is coated with ITO or conducting metal. Use of plates having only a single coated surface can facilitate the optical transmission of the device, a property that is often critical at ultraviolet or near ultraviolet wavelengths. One means of making the appropriate electrical contact involves placing a wire directly on the metal surface of the plate. This approach suffers from the difficulty of maintaining sufficient contact between the wire and metal coating on the surface to facilitate uniform electrical conduction, particularly when the device is subjected to repeated handling. To circumvent this, one can glue the wire to the metal coated surface using material obtained from Delta Technologies Limited, 13960 North 47th Street, Stillwater, Minn. 55082, USA. Alternatively, one can place a thin strip of metal on the conducting surface of the plate. This can also be glued in place. A preferred material for this can be purchased from Schlegel Systems, Inc., Rochester, N.Y. 14623, USA. One thin strip that is particularly useful is their Conductive Anti-Tarnish Copper Tape which comes in a variety of widths, contains one sticky surface, and is heat stable at 121° C., making it autoclavable. This permits construction of sterile sensors that can be used as cell culture growth chambers. The resistance between these tapes and that of the ITO surface of glass microscope slides purchased from Delta Technologies is less than 1 ohm. FIG. 1 shows one way that this strip can be located in the device. In this position, it permits good electrical contact between the surface of the optically coated material and a brass holder. Since the coating is present only on the ITO coated portion of the sensor, this portion of the sensor can be changed easily. This feature is particularly desirable when the sensor surface is to be produced in a fashion that makes it disposable. Using a doubly coated material permits the optical surface to be mounted tightly to the holder, a particularly desirable feature when the entire device is to be disposable.

The need to prevent electrical contacts between the two plates of the device shown in FIG. 1 can be met by introduction of an insulator between the two plates. It is often convenient to prepare this from a flexible material that permits a good seal such as a PDMS (polydimethylsiloxane) membrane or a silicone rubber gasket. This can be of nearly any thickness but it is preferable that it be similar in thickness to the sample being analyzed. The spacer can also consist of short posts and need not surround the sample as is shown in FIG. 1. The spacer can also be molded into one or both surfaces during production. The composition of the spacer or gasket will depend on how the device is to be used. For most uses, it should be made of a non-reactive insulating rubbery material that makes a good seal with the surface of the sensor and prevents fluid leakage. The spacer can be glued to one sensor surface, if desired to obtain a better seal. This creates a shallow open chamber that facilitates addition of the conducting fluid, the next step in assembling the sensor sandwich.

Electrical contacts between the sensor and the sample occur through a conducting fluid. This can be nearly any dilute buffer that is capable of conducting electricity. The pH of the buffer should be chosen to render the analyte charged such that it migrates towards the surface that is to be observed. This includes the surface that coated (Example 1) or that to which the analyte-detection complex will migrate (Example 2). The type of buffer to be used in the connecting fluid will vary with the sample being analyzed. Analysis of RNA transcripts can be analyzed using most neutral buffers, often with EDTA, a divalent cation chelator that can reduce RNase activity. The use of a conducting fluid that contains a small amount of 0.3-1% agarose is often helpful for maintaining the alignment of the analyte and cells in the tissue section. Agarose that is suitable for this use, including low temperature melting forms, can be obtained from many commercial suppliers including FMC 191 Thomaston St., Rockland, Me. 04841 (USA).

Following the addition of the sample and conducting fluid, the two component surfaces of the sensor device are then joined to create a "sandwich" such that their conductive surfaces are brought into contact with the fluid. In this position each conductive surface of the sensor contacts the conducting fluid and, in some cases, the sample. Each surface is separated from the other by the insulating membrane as shown in FIG. 1. The sandwich is held together by a spring or clamp that is designed for this purpose. Care should be taken to prevent the introduction of bubbles into the sensor as the surfaces are being pressed together. If present, these can be removed by holding the sandwich sideways and inserting a syringe and needle through the gasket while holding the sandwich together loosely over a paper towel or other adsorbent material. Air and excess buffer will emerge between the plates and flow into the adsorbent. When all air has been removed, the sample is ready for analysis.

Example 4

Sensors that can be Heated and Cooled

ITO and other metal coatings have a significant resistance depending on their thickness. For most applications the thickness and hence the electrical resistance of these layers will not be a major concern unless it impedes the optical clarity of the sensor since relatively little current flows through the sensor during its operation. The passage of larger amounts of current through metal coatings can be used to heat the sensor, however, and a preferred means for doing this using glass slides that are metal coated on both surfaces is shown in FIG. 7. Slides that contain two ITO coatings can be purchased from Delta Technologies. They are arranged in the device such that the ITO that is not in contact with the conducting buffer is used for resistance heating by applying a voltage along the length of the sensor surface. Since this surface does not contact the conducting fluid, this applied voltage does not affect operation of the sensor other than to provide heat. One or both surfaces of the device can be heated in this fashion. The design shown in FIG. 7 illustrates a format that can be used to heat both surfaces of the sensor.

Heating the sensor prior to, or during, its operation can facilitate analysis. Heating prior to analysis can help disrupt the cell membranes in the tissue, thereby enhancing migration of the analytes to the sensor surface and/or facilitating interactions between the analytes and the detection reagents. Heating can also contribute to the specificity of nucleic acid detection. For example, the temperature stabilities of oligonucleotides as a function of ionic strength are well known. Single base changes can result in a substantial change in the stability of an oligonucleotide pair. By heating the sensor surface, the interactions between mRNA and the molecular beacons or PNA can be controlled accurately. Brief heat treatment can also disrupt the molecular beacons in a transient fashion, enabling them recognize their "ligands" more rapidly.

Heating can also be used to examine the quality of the sensor surface before use. For example, when sensors that contain molecular beacons are heated above the beacon melting temperature, they will fluoresce. By measuring the amount and uniformity of fluorescence observed, one can monitor the quality of the coating. Since operation of the beacons is reversible, they will return to their non-fluorescent conformation when the sensor is cooled. Heating can also be used to distinguish non-specific and specific interactions during the analysis of mRNA and other nucleic acid hybridization assays when the sensor is used in the fashion described in Example 2. As the sensor is warmed, non-specific interactions between mRNA and the fluorescent PNA will be disrupted, preventing the transport of the PNA to the sensor surface. Precise control of sensor temperature can thereby facilitate identification of single base pair mismatches. This may be particularly helpful in identifying cells that contain mutations in only one allele.

It is also possible to incorporate mechanisms for cooling the sensor. Methods for doing this can be as simple as mounting the sensor on a Peltier heating/cooling stage or as complex as passage of a cooled fluid in a chamber that can be constructed beneath the lower sensor plate or above the upper sensor plate. By altering the temperature of the sensor, it is envisioned that it can be used for polymerase chain reaction analyses that can amplify the analytes being studied.

Example 5

Use of an Electrical Field in the Sensor

The sensor has been designed to be operated in the presence of an applied voltage. While it is conceivable that some analysis can be obtained in the absence of an electrical potential, the benefits of using an applied voltage greatly facilitate analysis sensitivity and speed. Application of an electrical potential to the device can accelerate the movements of analytes to the sensor surface, depending on their charges. This will result in enhanced speed and sensitivity of the measurements. The presence of an electrical potential can also cause disruption of cells and thereby permit detection of analytes that would otherwise be prevented from reaching the sensor surface. Many analyses can be performed under constant voltage conditions. It is not necessary for the voltage across the sensor be constant, however, and it will often be preferable to vary the voltage using patterns shown in FIGS. 4a,b or that are found experimentally to be best for a given measurement system. The type of polarization pattern to be used is highly sample dependent. That shown in FIG. 4a is sufficient to enhance interactions between nucleic acids and surface adsorbed molecular beacons. Further by varying the electrical potential in conditions when the sensor is being operated as described in Example 1, it is possible to maintain high concentrations of analytes near the sensor surface and, at the same time, prevent them from coming into direct contact with the metal oxide. Since in this location they will be in an ideal position to contact their binding partners such as molecular beacons, this can also speed the reaction.

Variations in the electric field can also facilitate analyses when the sensor is used as described in Example 2. In this case a variation in the surface charge similar to that in FIG. 4b is more appropriate. The use of a constant electric field has a tendency to promote the migration of negatively charged nucleic acids to the anode where the concentrations of fluorescent PNA detection molecules are low. By varying the charge on the sensor, the nucleic acids can be made to migrate through the portion of the sensor that contains the highest concentrations of PNA. Further if the PNA contain a moderate positive charge, variation of the potential can cause the paths of the nucleic acids and PNA detection reagents to cross many times. This will enhance the likelihood that they will interact and speed analysis.

The ability of the sensor to detect protein gene products can also be enhanced by the use of the electric potential. By operating the sensor at the appropriate pH, it is possible to separate protein isoforms that may otherwise interact with the same detection molecule. Many proteins can be phosphorylated, a phenomenon that also results in a shift in their isoelectric points. Thus, even if two proteins are recognized by the same fluorophore, they can be distinguished if one migrates towards the sensor surface and the other migrates away from the sensor surface at the pH at which the sample is being measured. They can also be distinguished if they are oxidized differently when they come into contact with the metal oxide coating.

Example 6

Use of the Sensor in a Flow Cell Arrangement as a Perfusion Chamber

When the sensor is assembled correctly, the sample will be contained within a small chamber the thickness of the gasket. It is possible to attach thin tubes or needles that act as "ports" to access the interior of the chamber within the gasket. One means of doing this is simply is to insert needles through the gasket. This permits perfusion of substances through the device. Furthermore, it is possible to utilize both surfaces of the device for observation. The cell can be used to rapidly optimize electrical polarization parameters for promoting interactions between the analyte and the sensor surface or materials attached to the sensor surface. Thus, in addition to its use as a sensor per se, it can be used to optimize the parameters needed for analysis of tissue sections in the device to be employed for this purpose such as that in FIG. 1.

Example 7

Total Internal Reflection (TIR) Illumination of the Sensor

Several methods are available for monitoring analytes in the sensor using TIR. As noted earlier TIRFM systems can be purchased from Nikon and Olympus Corporations. These enable illumination of the sample through either 60× or 100× high numerical aperture objectives that are in optical contact with coverslips that contain the samples. Use of these TIRFM systems requires that the surface used for analysis be a coverslip having a thickness of approximately 0.17 mm. They also require the use of an immersion oil to make optical contact between the objective and the coverslip.

Several other types of TIR illumination can be used for examining the sample. A preferred illuminator has the design shown in FIG. 6. This design permits the sensor to be used in TIRFM with a wider range of objectives. Indeed, it is possible to measure fluorescence in this arrangement using nearly any objective.

The illuminator functions by passing light from a laser through a rectangular lens having planar and convex surfaces. This lens is in optical contact with a triangular prism that is in optical contact with a 0.17 mm coverslip as shown. The prism can also be replaced by a cube as indicated by the broken lines in FIG. 6. These three components can be cemented together using Canada balsam or a suitable polymer or they can be held in optical contact using glycerol. The latter is often preferable since it will facilitate replacement of the coverslip. The most favorable arrangement of the lens and prism occurs when the focal point of the lens is at the junction of the end of the prism and the coverslip. Since all the light enters the coverslip below the critical angle, it will be totally reflected within the coverslip until it exits from its edge, which is adjacent to the surface of the sensor surface that is to be illuminated. The lens is chosen for its ability to expand the light from the laser in one dimension. As designed, the illuminator cannot be moved closer to the side of the sensor. Thus, the lens must be chosen to produce light that is sufficient to illuminate the entire width of the sensor.

The illuminator and the sensor are placed upon a microscope stage in a holder designed to keep the illuminator next to the side of the sensor. It is important that the illuminator not be joined permanently to the sensor, however. Microscopic observation across the width of the sensor is accomplished by moving the illuminator and the sensor in tandem as shown in FIG. 6. To observe fluorescence in other portions of the sensor, one moves the sensor along the illuminator, keeping the edge of the sensor in contact with the illuminator. By these means it is possible to scan the entire surface of the sensor. By adding appropriate motorized drivers, it is contemplated that scanning can be accomplished in an automated fashion. By keeping a computer record of the fluorescence observed, it should be possible to identify regions of interest without the need for immediate observation by the pathologist or surgeon. Retrieval of this positional information from the computer can facilitate human observation and speed diagnosis.

Example 8

Use of the Device with Standard Light Microscopy

The design of the device permits its use with standard light microscope techniques including phase contrast microscopy, bright field microscopy, darkfield microscopy, differential interference contrast microscopy, confocal microscopy, and epifluorescence microscopy. In most of these uses, the sample is illuminated by light that passes roughly perpendicular to the plane of the sensor. This permits examination of the entire sample, not just that portion that is adjacent to the sensor surface. By comparing the images obtained using these techniques with those obtained by TIRFM, it is possible to identify specific cells that contain the analytes being observed during TIRFM even though it is not possible to observe the entire cell using TIRFM.

The tissue sections can also be stained to increase the contrast between various cell types or organelles. This can be done using non-fluorescent dyes prior to TIRFM. It is also possible to use fluorescent dyes prior to TIRFM if the dye recognizes a substance to be analyzed or if the dye can be excluded from the evanescent field by application of the electric field. The advantage of using a dye before performing TIRFM is that it will facilitate correlating specific cell types with the location of the fluorescence. In some cases, however, it may not be possible to stain the tissue prior to TIRFM. In this case, it may be necessary to remove the non-sensor surface from the device to gain access to the tissue section. This can be facilitated by including a small layer of gauze between the non-sensor surface and the tissue section to prevent sticking of the surface to the tissue.

In some cases it will also be useful to employ the electrical potential that can be generated by placing a charge on the sensor surface to remove excess stain from the tissue section, thereby reducing the time needed for staining and clearing the background. This can be done by placing the sensor surface and its attached tissue section in a bath and applying a low voltage across the sensor surface and the bath.

Example 9

Use of Photobleaching within the Device

One of the limitations of using fluorescence to study gene expression is related to the number of fluorophores that can be distinguished at one time. Photobleaching can expand the measurement range, however. For example fluorescein and Alexa Fluor488 have about the same fluorescence spectra. The former is much more readily photobleached, making it possible to distinguish analytes that are labeled with fluorescein from those labeled with Alexa Fluor488 by the differences in the rates at which they are photobleached. The combined use of organic dyes and quantum nanodots, which are nearly impossible to photobleach should extend this technique further.

Example 10

Use of the Device to Measure Enzymes

Another use of the device is for measurements of enzyme levels in tissue samples. Many cancers have different levels of extracellular and intracellular proteases and these can be readily distinguished by use of fluorophores that contain protease cleavage sites. Cleavages at these sites by the actions of the specific proteases will cause the release of a quencher from the fluorophore resulting in fluorescent light emission. One of the advantages of the device described here is that it is possible to use the electrical potential to cause proteins and other molecules that are not nearly as negatively charged as mRNA and nucleic acids to migrate to a different sensor surface than the nucleic acids. This will permit simultaneous analysis of mRNA and proteins in the same sample. Application of similar approaches will permit the measurement of any type of enzyme reaction that can lead to the appearance or disappearance of fluorescence.

The ability of the sensor to detect differences in the net charge of a molecule can also be used in assays of kinases and phosphatases, enzymes that alter the phosphorylation status and charge of a molecule. For example it is possible to prepare fluorescent peptides that are substrates for various protein kinases. The presence of kinase activity in the sample can cause the fluorescent peptide analog to migrate to the anode whereas the non-phosphorylated analog may fail to migrate or may migrate to the cathode at the pH employed in the conducting fluid buffer. This will permit cell specific analysis of these important cellular enzymes, many of which have been implicated in tumorigenesis.

The ability of the sensor to detect differences in charge can also be used to detect protease activity. Fluorescent protease substrate can readily be designed such that proteolysis will change the ability of the fluorophore to migrate to either the anode or the cathode, where it is readily detected. This can be accomplished by adding charged amino acid residues to the substrate, which are then cleaved by the protease.

Example 11

Use of the Device to Measure Small Molecules

Binding of small fluorophores to proteins or larger macromolecules results in a loss of molecular mobility. When the small molecules are labeled with fluorophores, this will result in a change in fluorescence polarization that is readily detected. The device illustrated in FIG. 1 can also be used to monitor changes in fluorescence polarization and thereby be used to monitor the levels of small analytes in tissue sections. In this case, it is often desirable to coat the sensor surface with antibodies that are specifically capable of recognizing the analyte. One means of attaching the antibodies to the surface involves biotinylating them and then coupling them to the surface through a streptavidin bridge. Methods for biotinylation of antibodies and other proteins are well-known in the art.

Example 12

Use of Multiple Molecular Beacons to for Cell Classification

As noted earlier, data obtained using microarrays suggest that many mRNA will be elevated at the same time in cancerous and malignant cells. This phenomenon can contribute to the sensitivity of the device. Molecular beacons that are specific to multiple mRNA are coupled to the surface of the sensor surface as in Example 1. When these are labeled with the same fluorophore, they will detect the increase in any of these mRNA. Similarly, some populations of mRNA decrease in cancerous cells. By mixing these and labeling them with a different fluorophore than used in beacons to monitor mRNA whose expression is found to be unchanged and with a different fluorophore that used in beacons designed to monitor mRNA whose expression is found to be increased, it is possible to increase the sensitivity of the method. As noted earlier, it is also possible to make use of both surfaces of the device to increase the numbers of analytes that can be monitored. Similar types of mixtures can be employed for analysis of gene transcription produces using the sensor as described in Example 2.

Example 13

Use of the Device for Electrophoretic Separation of Samples in Three Dimensional Electrophoresis The principles shown in the device illustrated in FIG. 1 can also be applied to techniques other than analysis of tissue sections. One use of the device is to separate small quantities of materials by electrophoresis. For example, when the ends of the device are left open, it is possible to pass an electrical current from one end of the device to the other by attaching electrodes to each end. If the device is loaded with polyacrylamide gel or other medium used to separate proteins, nucleic acids, or other substances by electrophoresis, samples that are placed in the gel will separate according to their net charge/mass ratio. Thus, it will be possible to separate proteins by their isoelectric points in a gel that contains a pH gradient. It will be possible to separate proteins by their molecular weights in a gel that contains sodium dodecylsulfate (SDS). It will also be possible to operate the sensor in a two dimensional fashion by alternately passing current through the ends of the device and through the sides of the device. This will permit two dimensional analysis of trace quantities of analytes. Following separation, the separated analytes can be forced to migrate to one or both surfaces by passing an electrical current between their component metal oxide layers. When the proteins or analytes reach the surface they can be detected using fluorescence assays performed using the apparatus in a TIRF or TIRFM mode. One use for this procedure will be to analyze extremely small samples, such as the components of a single cell or nucleus. Once the locations of the analytes on the surface are identified by their fluorescence of their influence on the fluorescence of materials attached to the surface, they can be removed and identified further by mass spectroscopic or other methods.

Example 14

Use of the Sensors in a Microtiter Well Plates

Figure 8:
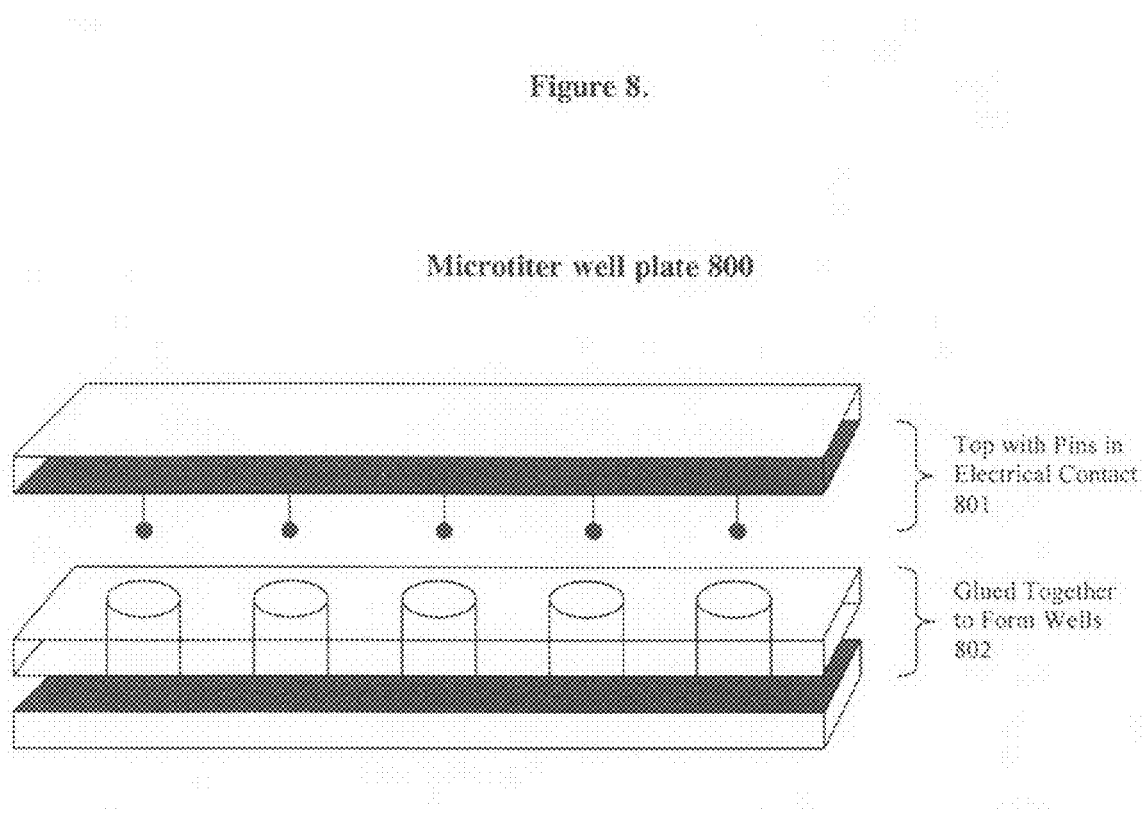
FIG. 8 illustrates a microtiter well plate design.

Microtiter plates are often used for analysis and the application of an electrical potential to this assay format can facilitate analysis. For example, it can be used to increase concentration of an analyte at the plate surface. It can also be used to reduce the concentration of an analyte at the plate surface. Many of the applications of the sensors except for those that involve tissue sections can be transferred to a microtiter well plate format. These include enzyme assays and nucleic acid assays. Several formats can be used to build microtiter plates that can be used with electrical potentials. One of these formats is illustrated in FIG. 8.

Example 15

Sensors with Permeable Optical Polymers

Polymeric Hydrogels

One of the limitations of the sensor shown in FIG. 1 is related to the location of the electrodes, which limitation consists of the ITO coating on the glass surfaces. These coatings are situated between the surface of the specimen being examined and the optical surface. While the metal interferes only slightly with the optical quality of the surface, the fact that it contacts the fluid between the sample and the area where the sample is being examined limits the amount of voltage that can be applied. This voltage should be kept below that which will cause electrolysis of water, a phenomenon that will produce bubbles and interfere with migration of the analytes thereby hindering analysis. Furthermore, an excessive potential can have a negative impact on the analyte if the analyte contacts the metal electrode surface, which is almost certain to occur. This limitation on the amount of voltage that can be applied in the device can impede the analysis by preventing efficient and uniform extraction of material from the cells. It would be preferred to locate the metal electrodes on the opposite surface of the glass from that shown in FIG. 1 where electrolysis of water would not interfere with analysis and the sample would not come into contact with the charged metal coating. Unfortunately, however, doing so can interfere with the uniformity of the electric field near the optical surface, a phenomenon that can cause uneven migration of the analyte. As a consequence of placing the electrode on the opposite surface of glass from that shown in FIG. 1, the uneven deposition of analyte on the optical surface may interfere with the correlation of the distribution of the analyte on the glass surface with that in the tissue section.

The voltage limitation of the sensor can be overcome by replacing the glass optical components of the sensor with permeable optical polymers (polymeric hydrogels) that are permeable to ions and placing the polymer between the sample and the electrodes as shown schematically in FIG. 9A. Consequently, the electrolysis of water will not interfere with the analysis and the analytes will not come into contact with the electrodes. This will permit the use of greatly increased voltages for electroporation of analytes from the tissue section and migration of analytes to a region where they can be analyzed. Permeable optical components (i.e., those that refract light) can be made of a variety of polymers. The properties of these polymers are well known and have enabled the construction of contact lenses that can be worn for extended periods. Furthermore, these polymers can be designed to have many chemical features that will facilitate their use in the sensor. For example, they can be composed of materials that have either a net positive or net negative charge or that have the capacity to buffer the pH of the area in which they are located. This can be used to alter the charge of the analyte and change its mobility within the device. These polymers can also be designed to have a refractive index that will enable the use of total internal reflection, a property that renders them useful for the analysis of trace amounts of materials including analytes from tissue sections.

The use of polymeric materials has another major advantage as well. It permits the design of components that include aqueous solutions that can be stored in sealed pouches. This frees the operator from having to add water or buffers. This is important because it lessens the potential for mistakes to be made. When tissue sections are being made during surgery, time is of the essence. The fewer operations that are required, the less likelihood that mistakes will be made. Furthermore since, the fluid components are within the gels, it reduces the chances that bubbles will be introduced between the tissue sections and the components of the sensor when assembling sensor components, a process likely to be done manually by the person cutting the tissue sections.

The overall principles that underlie the operation of a polymer-based sensor are the same as those that are responsible for the operation of the sensor in FIG. 1. In both devices, the analysis depends on the use of an electric field to cause analytes to mix with a detection reagent to form a complex that can be detected optically. The design of the polymer-based sensor illustrated in FIG. 9 differs from that in FIG. 1 in the location of the electrodes relative to the optical surface that is being used for detection. In FIG. 1, the electrodes are between the sample and the surface. In FIG. 1 the optical surface is between the sample and the electrodes. Another difference in the sensor illustrated in FIG. 9 and that in FIG. 1 is that the optical surface in FIG. 9 permits current to flow through it; that in FIG. 1 blocks the flow of current.

The use of polymers in the design of the sensor in FIG. 9 permits it to be constructed in a modular fashion. As shown in FIG. 9B, the sensor can be arranged into two parts, which will be termed the anode and cathode sensor assemblies to reflect the assembly that will contact with the anode and cathode respectively. These can be marked with a color code, e.g., red for anode and black for cathode, to make them more easily distinguished. This is particularly useful when they contain polymers that differ in composition and/or buffer content. There is no particular order in which the sensor needs to be assembled in most cases or for the anode assembly to be on the bottom and for the cathode assembly to be on the top. Thus, the sample can often be applied to the anode sensor assembly before addition of the cathode sensor assembly. It is usually best to do all the operations in the same fashion, however, to avoid making mistakes such as using two anode assemblies or two cathode assemblies when the compositions of these are not identical. The chances for making this mistake are reduced by the design of the apparatus that is to be used for electrophoresis, which is incapable of being loaded with two anode or two cathode assemblies. Furthermore, the design of the anode and cathode assemblies (FIG. 9D) and this box (FIG. 9C) makes it impossible for the anode and cathode assemblies to be reversed.

The anode sensor assembly contains the polymer that will be the primary site of analysis when RNA gene products are to be examined from tissue sections since this is the direction in which these gene products will migrate during electrophoresis. This is identified as component #3 in FIG. 9A. The polymer that is located adjacent to this, that is shown as component #4 in FIG. 9A, is where most of the combination of the RNA and the detection reagent will occur. The polymer in component #4 is usually of a lower refractive index than that used to construct component #3 since this will permit illumination of the polymer in component #3 by total internal reflection. As a result fluorescent material that remains in component #4 will not be illuminated and, therefore, not interfere with the analysis. Since the ability of the polymers in component #3 and #4 to buffer the pH can be made to differ, this property can be used to alter the net charge on the fluorescent detection reagent and thereby prevent it from entering the polymer in component #3 unless it is bound to negatively charged RNA. For example, if the detection reagent has a net positive charge at the pH of the buffer in component #4, it will migrate towards the cathode and cross the path of the RNA that is migrating from the tissue section towards the anode. This will increase the sensitivity of the method by minimizing the background due to the presence of unbound detection reagents. It will also permit the use of larger concentrations of detection reagents, which will increase the chance that they will interact with species of RNA that are being measured.

When the sensor is being used to measure RNA and no other gene products, virtually all the measurements will be made on the part of the sensor shown as component #3 in the anode assembly (FIG. 9). This simplifies the design of the cathode assembly, which can consist of a single polymer, a spacer (component #8) and the electrode (component #9). The primary function of the cathode assembly in this case will be to deliver voltage across the device. It should be noted, however that the cathode assembly can also be used to make measurements of analytes that are positively charged. In this case one will want to include a polymer that can be used for optical analysis as outlined in FIG. 9. Furthermore, it is possible to use the cathode assembly to facilitate staining of the tissue sections with positively charged dyes. The polymer to be used in the cathode assembly should be of optical quality even when it is not being used for analysis, however. This is to permit visualization of the tissue section after electrophoresis and analysis of the RNA is complete, a requirement that will become clear later.

It should also be noted that sensors can be made with molecular weight cut off devices by inserting a piece of dialysis tubing between the polymers. When these are placed between components #2 and #3, all the high molecular fluorescent species will be collected at a surface that can be made very thin to permit better detection (c.f., component #2a, FIG. 9A). The dialysis tubing is useful for RNA analysis since it prevents it from passing through component #3 and being lost.

The sensor also contains other components that are not optical polymers or even polymers but that are present to facilitate delivering an electrical potential to the sensor. Components #1 and #9, which serve as the anode and cathode, respectively, are designed to create an electrical potential across the device. Components #2 and #8 can be incorporated into the anode and cathode as shown in FIG. 9D. The anode and cathode elements shown in FIG. 9D are constructed from a thin strip of conducting metal, which serves as the back and a molded piece of clear plastic, which serves as the bottom and sides. A piece of sintered polyethylene is used to make the front and after the device is loaded with fluid, to create the top cap. The sintered polyethylene frit at the front provides the support needed for the polymer gel (i.e., either component #3 or #7 shown in FIG. 9A). The top of the device is surrounded by a piece of heat shrink plastic to seal this portion of the device. This is removed during use although in some cases the amount of bubbles is not sufficient to increase the pressure in the electrode components to a point in which it interferes with analysis. In this case, it is not essential that the heat shrink plastic be removed.

Figure 9E:
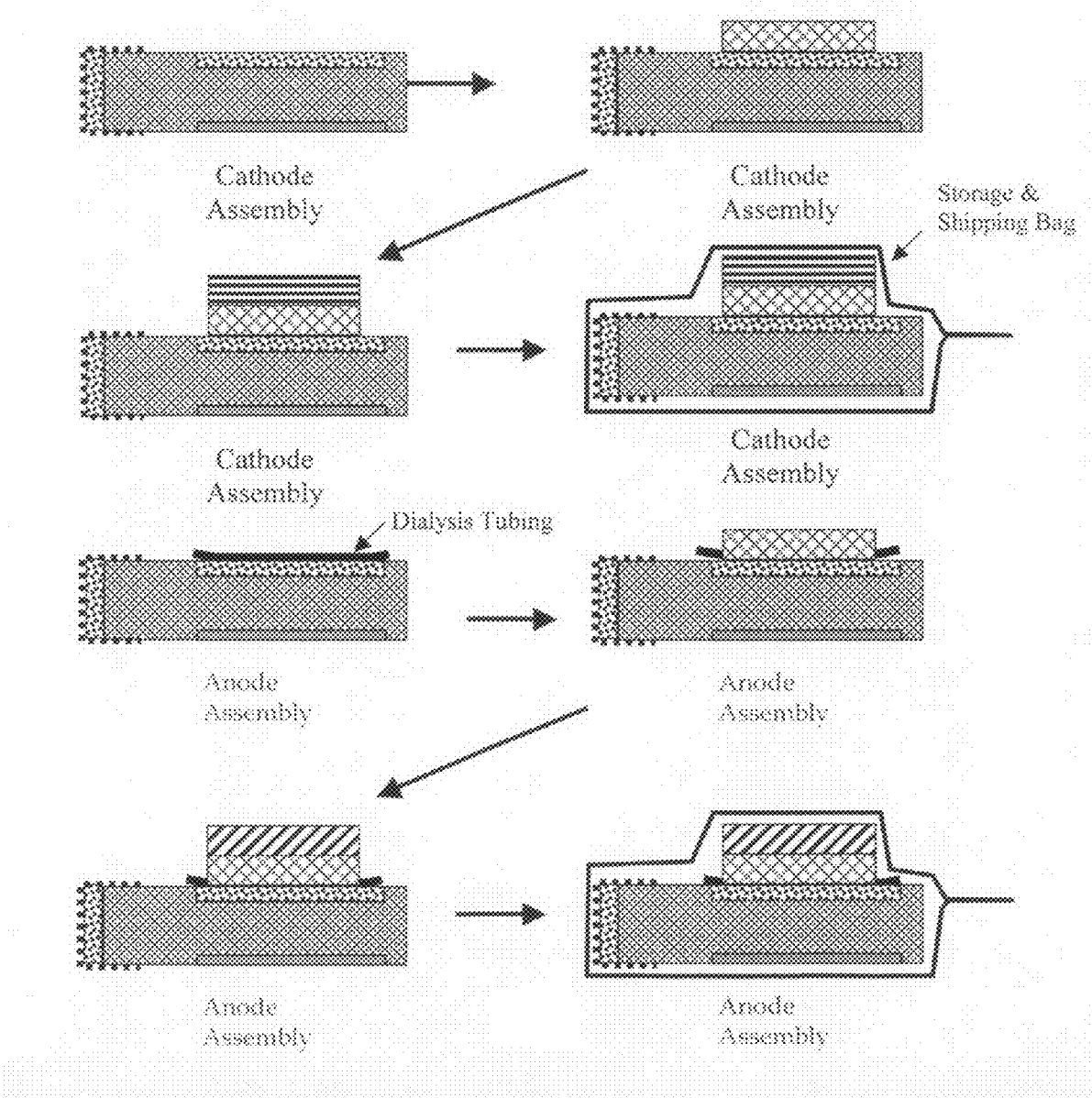

The final steps in the construction of the anode and cathode assemblies involve layering the polymers illustrated as components #3 and #4 and components #6 and #7 on the anode and cathode respectively. This is shown in FIG. 9E. Note that when RNA species are being monitored, it is useful to insert a piece of dialysis tubing between the anode and component #3. This can also be accomplished by polymerizing component #3 on top of a piece of dialysis membrane having a pore size sufficient to block the migration of RNA. This will trap any RNA-fluorescent complexes that are migrating through component #3. Further, since this can be quite thin, it can increase the resolution of the device. The presence of the dialysis tubing is not essential, however. Several other means of trapping the complex are also possible and these can be attached to the polymer. Once the gels have been added to the device as seen in FIG. 9E, then the device is enclosed in an airtight bag. A few drops of water or, preferably, a water-saturated piece of towel is added to make certain the device remains moist until use. All steps in the preparation of the assembly should be done under clean conditions to prevent bacterial or other contamination. Also, since the device will be used to measure RNA, care should be taken not to contaminate the device with RNase. This means that persons assembling these components should be wearing gloves and taking standard precautions for working with RNA containing materials. The device can also be sterilized by ethylene oxide before the bag is sealed to prolong the half-life of the assembly.

Use of the sensor device requires only a few simple steps. Either the anode or cathode assembly pack is opened at the time of sectioning or a section is placed directly on the exposed gel. When this is opened just prior to use, there should be sufficient moisture to give good contact of the tissue section to the gel. It is important that no air be trapped between these sections, however, since this can interfere with RNA or other analyte extraction from the tissue. A few drops of sterile water can be added at this time to avoid this problem, if needed. Once the section has been placed on the anode or cathode assembly it is covered by a cathode or anode assembly, which is placed on top of the section such that its gel contacts the section. It is a good practice to begin with either the anode assembly since it is easy to see how the tissue section contacts the polymer and since this contact is the most important. Then, one adds the cathode assembly such that its gel side faces the tissue section. Again, a few drops of water might be needed, but this should not be necessary if the assembly package is opened at the time of use and if it has stayed hydrated.

Once the sensor sandwich has been assembled, it is ready for the electrophoresis step. The sensor sandwich is inserted into the electrophoresis chamber as diagrammed in FIG. 9C. The cutouts on the sandwich prevent the electrode from being inserted into the electrophoresis box in an improper orientation. They also guard against mistakes in assembly such as the preparation of the sandwich from two anode assemblies or two cathode assemblies. The electrophoresis is performed at voltages of up to 100 volts/cm. The actual voltage used will depend on the tissue with soft tissues requiring lower voltages than tissues that contain substantial amounts of connective tissue. It is often useful to use a transient voltage that is very high to cause electroporation of the cells, which will release the RNA. The limit to the amount of voltage that can be employed depends on how the tissue is to be examined after the gene products have been detected. The use of very high voltages tends to destroy the tissue, making it more difficult to study after electroporation. This can be reduced by the inclusion of small amounts of detergent in the polymer layers that are in contact with the tissue section.

Following electroporation and electrophoresis, the sample is ready for visualization. This is done by removing the sandwich from the electrophoresis box and, in the case of negatively charged analytes such as RNA, observing the fluorescent material that is collected in the portion of the sensor in components #2a or #3 (FIG. 9A). As seen in FIG. 9F, anode components #1 and #2 are removed from the sandwich. The sandwich is then placed on top of a fiber optic window or a fiber optic taper that is covered with a piece of Dupont FEP film or other film of low refractive index. It can also be covered with water when a dialysis membrane is included, but this can risk contamination of the window or taper. This can be avoided by covering it carefully with some microscope immersion oil and a thin coverslip, which can be replaced if it gets contaminated. The presence of a low refractive index material between the sensor and the window or taper is required to minimize unwanted stray light entering the detector from the illumination source. Mounting a cutoff filter beneath the FEP film can also reduce the stray light, but this will also lower the sensitivity of the device. The other end of the fiber optic window or fiber optic taper is mounded on the sensor chip of a charged coupled device (CCD). Mounting is performed in such a way that the dialysis tubing (when present) or component #3 is in contact with the Dupont FEP film directly on top of the fiber optic. The sample is illuminated through the side of component #3 using lasers or other light sources that have the appropriate wavelength. Due to the fact that the refractive index of component #3 is greater than that of the adjacent polymeric gel or the Dupont FEP film, the excitation wavelengths will be reflected within the gel internally where it is capable of illuminating fluorescent material that has become associated with the analyte. Consequently, none of the unreacted fluorophore detection reagent that remains in other portions of the apparatus will be illuminated and all will remain invisible.

Example 16

Sensors with Peptide Nucleic Acids

PNA

A desirable detection reagent for a nucleic acid is a molecule that has bases that are held in an ordered fashion such that they can form Watson-Crick base pairs with nucleic acids and that lacks the negative charges in the backbone atoms that hold the bases in order. This is because the negatively charged phosphates of nucleic acids exert a repulsive effect on formation of the oligonucleotide duplex. By replacing the negatively charged phosphate atoms with atoms or groups of atoms that have either no charge or that have positive charges, one can devise detection reagents that will have high affinity for specific oligonucleotide sequences. Indeed, the affinities of these can be greater than that of nucleic acids for complementary nucleic acids.

PNA are molecules capable of forming Watson-Crick base pairs with nucleic acids that have a peptide backbone. Because they lack the negatively charged sugar-phosphate backbones found in RNA and DNA, hybrids of RNA-PNA and DNA-PNA are known to be highly stable [24]. PNA can be constructed to be essentially uncharged, negatively charged, or positively charged simply by incorporating amino acids into their backbones by standard peptide synthesis chemistry. PNA have also been labeled with fluorophores [18,21] and used to detect nucleic acids by fluorescence in situ hybridization (FISH). PNA are not the only structures that can be used for this purpose, however. Agents in which the phosphate is replaced by sulfur or carbon are also useful.

When PNA are bound to nucleic acids, they can alter its mobility [20] in gels or in capillary electrophoresis tubes [17]. The ability of DNA to change the charge of PNA such that its migration in an electric field is reversed has not been employed, however. This is a particularly important property for use in a sensor of the type taught here in which it is preferable for the electrophoretic migration distance to be relatively short. Binding of uncharged or positively charged PNA to RNA or DNA will cause it to become negatively charged. As a consequence, the complex will migrate in the opposite direction from the uncomplexed PNA in an electric field. This can be used to separate bound PNA from non-bound PNA. If the PNA is labeled with a reagent such as a fluorophore, a radioisotope, biotin, or other molecule that does not cause it to acquire a net negative charge, then binding of the labeled PNA to nucleic acids will cause it to be separated from the non-bound PNA. This provides a very useful and simple tool for the identification of nucleic acids. Further, this permits the labeled PNA to be employed at very high concentrations, which facilitate its interactions with nucleic acids without increasing the background signal when the signal is measured by a technique such as total internal reflection fluorescence of TIRFM. In addition, this property can be used to cause nucleic acids or other charged materials to migrate into areas where they can be assembled into complexes.

Because PNA have a peptide backbone and can be synthesized similar to peptides, it is possible to incorporate several different types of labels into them. For example, it is possible to add cysteine residues to PNA that will permit labeling of the molecule with fluorescent probes that react with thiols or that can be made to react with thiols. Many such probes are available from Molecular Probes, Eugene, Oreg. It is also possible to incorporate lysine molecules into PNA. This will give them a positive charge or serve as a labeling site for amino reactive agents. These are also available from Molecular Probes in a wide variety of absorption and emission wavelengths. One can incorporate arginine residues into PNA to alter their charges as well. PNA have also been labeled with histidine residues [24]. The pK of the imidazole moiety of histidine can have a favorable influence on the migration of PNA in an electric field that has a pH gradient. For example, at low pH, histidine is positively charged. At high pH, it becomes uncharged. A PNA that contains histidines will tend to migrate away from an anode when it is in a low pH environment. Its mobility will be reduced as it reaches a higher pH environment due to the loss in charge. Thus, one can easily devise conditions in which histidine labeled PNA migrate away from an anode until they reach a region of an electrophoresis chamber in which their migration becomes slow. One use of this is to drive the PNA to a region of the chamber away from the anode but prevent them from migrating to a region where they would be unable to react with oligonucleotides. PNA that have bound to oligonucleotides will migrate back towards the anode away from their non-bound counterparts.

The design of PNA is relatively straightforward and is based on the notion of Watson-Crick base pairing [24]. The fact that PNA are uncharged or can be made positively charged enables them to invade short RNA-RNA duplexes found in most gene expression products. Increasing the temperature of the device can facilitate this. The usual length for the hybridization reaction is 16-25 bp. The only other considerations in designing the PNA relate to the solubility of the molecule. Long uncharged PNA are generally not soluble and are not well suited for use in the sensor. Positively charged PNA are much more soluble and much better suited for the measurements with the sensor, particularly if their charges can be modulated as a function of pH, e.g., by addition of residues such as histidine when they are employed at pH values in the range of 6-8.

A key to the operation of the sensor is its ability to maintain a very low background. This enables the detection of trace quantities of RNA analytes. As just discussed, the use of PNA and the ability to reverse the migration of labeled PNA molecules in an electric field is one means of maintaining a low background. Another method of reducing the background is to use PNA that have a hairpin conformation similar to that found in molecular beacons. In the PNA hairpin conformation [23], which is found before the PNA is complexed with an oligonucleotide, the fluorophore at one end of the PNA is quenched by a molecule that is attached to the other end of the PNA by resonance energy transfer. This occurs due to the proximity of the fluorophore and the quencher, which are near one another only when the PNA has a hairpin conformation. Binding of the PNA to RNA causes the hairpin to become linear, which results in the fluorophore being moved from the quenching agent. As a result, the fluorescence becomes visible and can be observed. Since formation of the hairpin shape does not alter the isoelectric point of the PNA before it is bound to RNA, the hairpin shaped PNA will also migrate away from the anode. This will change when it interacts with RNA, however, the time that the fluorescent PNA-RNA complex will be migrating towards the anode. These movements are illustrated schematically and described in FIG. 10.

Another important means of reducing the background fluorescence is the use of total internal reflection optics. By restricting the illumination to the components of the sensor that contain the fluorescent RNA-PNA* complexes, it is possible to prevent illuminating the uncomplexed PNA*, which would contribute to the background. It is desirable to illuminate only component #3 in the sensor. This can be done if component #3 is transparent to the illuminating radiation, if component #3 has a higher refractive index than component #4, and if component #3 is illuminated at an angle less than the critical angle. This can be calculated from Snell's law from the refractive indices of components #3 and #4.

The requirement for total internal reflection illumination of component #3 can be met using polymers that have been designed for the construction of soft contact lenses that are intended for long use. These have been designed to be sufficiently porous to enable air and fluids to pass through the lens where it can reach the cornea. Further, their refractive index is sufficient to bend light needed for vision correction. The refractive index of these materials has been shown to permit their use for total internal reflection fluorescence [22] as would be expected from their refractive indices.

There are several materials that have been used to construct contact lenses. Two of the most common are HEMA (hydroxyethylmethacrylate) and HEMA-MAA (HEMA-methacrylic acid). Commercially available lenses of the former have a refractive index of approximately 1.437 and contain 42% water. Commercially available lenses of the latter have a refractive index of approximately 1.407 and contain 55% water. The latter are also much more permeable and have significantly larger pore sizes. Thus, these materials are suited for both total internal reflection in aqueous buffers in which the refractive index is approximately 1.33-1.37 and for electrical conduction needed for electrophoresis. Both types of polymers can be readily molded and made sufficiently thin for use in the device and are commonly made in sizes in the range of 0.2 mm. Due to the desirability of having the most resolution possible, it is important that the thickness of component #3 be kept relatively small, in the order of 0.2 mm. The thickness of component #4 should also be kept small, but this is not as important as that of component #3, which is the component that will be illuminated. Since component #4 is not to be illuminated, its composition is much less critical than that of component #3. In fact the composition of component #4 can be virtually any soft gel that can be molded into a shape that will fit between component #3 and the tissue section. The critical features of component #4 are that it permit migration of RNA, PNA*, and RNA-PNA* complexes and that it have a lower refractive index than component #3 to permit component #3 to be illuminated by total internal reflection fluorescence. Thus, it is even possible to use a low percentage polyacrylamide or agarose gel for component #4. The use of polyacrylamide also permits the incorporation of immobilines into the gel during polymerization [25,19]. These should be chosen to buffer the local pH such that PNA* will be positively charged and will migrate towards the tissue section and away from component #3. The immobiline to be chosen, if one is to be used, would depend on the design of the PNA*, which will depend on the RNA to be monitored. In general, it is most useful to chose an immobiline that will buffer the pH of component #4 to be at least 0.1 pH unit less than the pI of the PNA*. The pH of the solution that is in components #1-3 should also be lower than the pH of the immobiline in component #4.

When RNA is the only cellular constituent to be analyzed, the composition of components in the cathode assembly is not nearly as critical as those of components #3 and #4. In general, components #6 and above should be at a pH that is equal to or greater than that of component #4. These can be fabricated of polyacrylamide or HEMA-MAA. When component #7 is to be used for total internal reflection, it is better to construct it of HEMA. It will be subjected to the same considerations as those discussed next for component #3. Note, that when an immobile is not used, the buffer throughout the sensor should have a pH that lower than that of the pI of the PNA*.

The design of component #3 should be considered carefully since this is the component of the sensor that will be illuminated and used for detecting the sample. As a rule, component #3 should be a hydrogel having an optical density greater than that of the buffer on either side of it and greater than that of component #4 to permit its illumination in a total internal reflection fashion and since it should be capable of transmitting an electrical current. This is a property that is also found in most soft contact lens hydrogels such as those that contain HEMA. Methods for preparing polymeric hydrogels containing HEMA and other substances are well known in the art and more than 700 patents related to the fabrication of these types of polymers were obtained by searching the United States patent data base with the terms "HEMA" and "contact lens." Particularly useful United States patents are U.S. Pat. Nos. 6,447,118, 6,552,103, 6,582,631, and 6,623,747, which describe methods for molding and modifying hydrogels that can be used to prepare component #3 in the sensor using an appropriate mold. It should be appreciated that nearly any hydrogel material that is has a refractive index that is sufficiently greater than the buffer to be used to permit total internal reflection of light, that has the ability to conduct an electrical current, and that is optically clear at the wavelengths of light used for illumination and fluorescence will be appropriate for use in sensor component #3 and for use in sensor component #7 when the latter will also be used for analysis and illuminated by total internal reflection.

Figure 11:
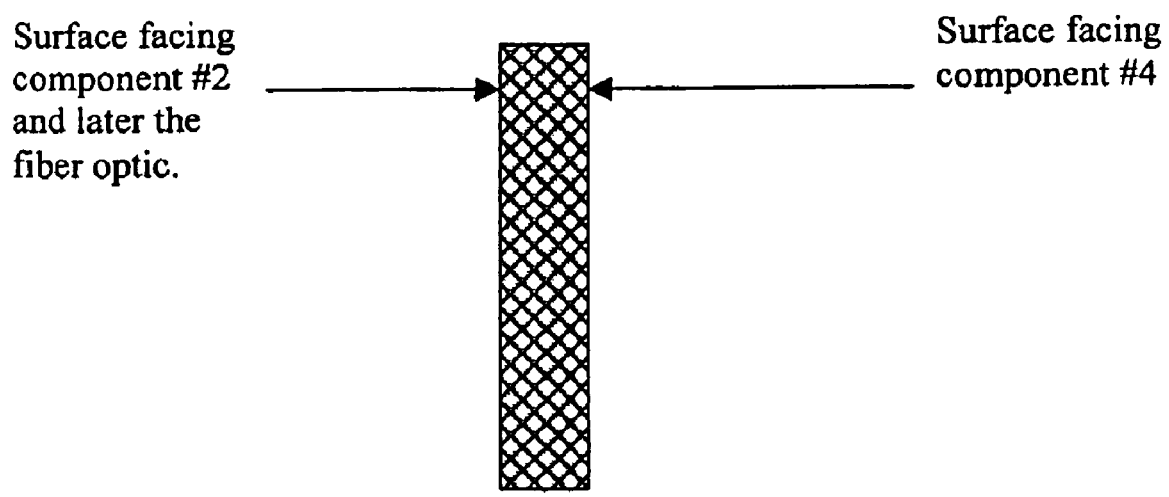
FIG. 11 illustrates design considerations for component #3.

Several aspects of component #3 can influence on the operation of the sensor. For example, when PNA having positive charges are used to detect RNA, it is useful to make the surface of component #3 positively charged. This will facilitate migration of non-complexed fluorescent PNA away from the surface of component #3 into areas of component #4 that will not be illuminated by total internal reflection fluorescence. When the sensor is used to detect RNA, it is also useful to fabricate component #3 from a hydrogel that has a smaller pore size. This will enable component #3 to behave in a semi-permeable fashion and thereby prevent the RNA-PNA* complex from migrating through it. This will avoid the need to attach materials to component #3 that are capable of binding nucleic acids or to use a semi-permeable membrane such as component #2a (FIG. 9A). Since hydrogels that have smaller pore sizes and that contain less water have an increased refractive index, this can facilitate the design of total internal reflection optics that will be used during analysis. Another aspect of the design of component #3 relates to its surface that faces component #2. When the detection system will involve the use of a fiber optic window or a fiber optic taper, component #3 may come into contact with the fiber optic. Since the fiber optic will also have a high refractive index, this could create the potential for the light being used for illumination to pass directly into the fiber thereby causing a high background and possibly preventing detection of light from the RNA-PNA* complex. Thus, it is essential to have a thin layer material of lower refractive index between component #3 and the fiber optic. This can be provided by placing the Dupont FEP film between the fiber and component #3. It can also be provided by a thin layer of buffer that can be attached to the surface of component #3 that will be nearest the fiber optic. For example, if the fiber optic is coated with a hydrophobic silicone monolayer such as Sigmacote purchased from Sigma Chemicals (St. Louis, Mo.), the surface of component #3 facing the fiber optic can be designed with an oligosaccharide coat to retain a small layer of water that will separate it from the fiber optic. This is sufficient to cause total internal reflection from this surface. These properties of component #3 are indicated in FIG. 11.

Following completion of the electrophoresis, it is necessary to detect the fluorophores that are bound to the surface of component #3 or, if the pores of component #3 are sufficiently large, that have traversed component #3 and accumulated on component #2a. This can be accomplished using an illuminator that is focused on the side of component #3 as seen in FIG. 9. Lasers are the most useful types of illumination for this purpose since they can be used as a source of coherent monochromatic light that can be focused to a small size. When more than one color of fluorophore is to be examined, the type of illumination that is to be employed will depend on the manner in which the signal from the sample is to be detected. When this is a camera based detector that employs that has a fiber optic window or a fiber optic taper, it is useful to employ an illuminator that is capable of illuminating component #3 at multiple wavelengths. This is because it is important to keep the distance between the fiber optic and component #3 as small as possible, making it desirable not to insert different filters between the sample and the fiber optic. To detect multiple colored fluorophores, one would employ multiple lasers or a dye laser that can be used with different dyes to produce desired wavelengths. By illuminating with the longer red-most wavelengths followed sequentially with wavelengths that are increasingly shorter, it is possible to obtain multiple pictures of the sample and to resolve these into different colors. A diagram showing this is illustrated in FIG. 12. A camera-based detector that employs an objective to monitor the fluorescent samples that are illuminated in component #3 is readily adapted for use with filters. Thus, one can vary both the excitation wavelength and the emission wavelength. The advantage of the fiber optic based system is that it recovers much more of the fluorescent light and can be designed to detect fluorescence from the entire sample at one time. This increases the sensitivity of detection and speeds the analysis substantially. This is usually sufficient to offset the greater flexibility gained from the use of emission filters that are more easily introduced into the objective based design.

Once the fluorescent image of the gene products has been captured, components #8 and #9 can be removed (if they have not already been removed) and the remainder of the sensor sandwich can be transferred to a light microscope. This permits visual inspection of the tissue section, if desired. Alignment of the section with the fluorescence image can be made by comparing the position of component #3 while the section is on the microscope stage with that while it was on the fiber optic. This is because the position of the tissue section will remain constant with regard to the position of component #3.

The sintered materials that can be used to make components #2 and #8 can be obtained from SPC Technologies Ltd., 1 Raven's Yard, Nethergate Street, Harpley, Norfolk, PE31 6TN, UK.

DETAILED DESCRIPTION OF THE FIGURES

FIGS. 1A-1C illustrate an overview of the sensor device showing the sensor from three different perspectives. FIG. 1A shows an end view of the sensor device 100. Sensor device 100 comprises tissue sections or other analytes 101, brass or other conductor 102, conducting tape 103, ITO or SnO2 coated slides 104, gasket insulator 105, matrix (including buffers) 106, microscope objective 107, CCD camera or other detector 108, and voltage generator 109.

Since a primary use for the sensor will be microscopy, the example shown here is constructed from microscope slides. There is no reason that larger or smaller sensors cannot be made, however. The sensor can also be constructed of 1 mm thick slides, a common size for microscopy, coverslips that are 0.17 mm thick, a common size for microscopy, or from a combination of the two. Indeed, since the device is likely to be observed by TIRFM, a preferred construction would involve the use of a coverslip for the portion of the sensor most likely to be viewed using TIRF. When RNA gene expression products are to be examined, this will be the anode. The view in FIG. 1A is of the sensor from the end. The slides (shown in solid gray) are coated with ITO, $SnO_2$, or other conductive metal. The thickness of this layer is not critical as long as it is thick enough to conduct current and thin enough to permit tissues to be viewed. The location of the coating is illustrated as a red line. It can be difficult to attach electrical leads to the metal coating of the slide. To make the sensor more robust during handling needed to load it with tissue sections, it has been designed to fit into metal holder that is made of brass or other conductor (gray oblique lines that rise upwards). The thickness of this holder is not important to the function of the sensor but should be sufficient to withstand rough handling in an operating room setting. The leads that control the potential on the device (black lines) are soldered or otherwise attached securely to the brass conductor. Contact between the metal coating and the conductor is made via a brass tape that is wrapped around the electrode (black rectangular shape). This is held to the slide by a glue that is stable in the autoclave, enabling the device to be sterilized. The two portions of the sensor are separated by a gasket (green), which serves as an insulator. The composition of this gasket is not critical but it is best if it is of a rubbery consistency, which makes it easier to use and to keep the device from leaking. Gluing the gasket to one sensor makes the device easier to load. Several other designs are possible so long as they result in a device that is able to deliver an electrical potential across the tissue section (shown in speckled contrast). Observation of the material can be from the bottom as shown here or from the top.

FIG. 1B shows a top view of the sensor device 100. Sensor device 100 comprises brass or other conductor 102 (Note that this has a shape that permits it to contact the conducting tape with which it forms an electrical contact and at least one of the conductors has a hole that permits observation of the metal coated slides and the material that is sandwiched between them), ITO or SnO2 coated slides 104 (Note that the tape is folded around the edge of the slide such that it makes contact with both surfaces), and gasket insulator 105 (Note that this shape permits it to contact the conducting tape on the sides of the device and, in cases in which a fluid is present, the slides at the end of the device).

The sensor contains at least one and preferably two optically transparent components. These are covered with a tape that is folded around the sensor as indicated in the first image of the top view. Other methods of attaching the electrical contacts will also work, but this design was chosen for its robustness, high conductivity, and ease of construction. Note that the conducting tape lies along the top and bottom of the entire sensor surface to facilitate even electrical contact with the metal oxide layer and the brass conductor. The edge is not coated throughout most of the slide, however, leaving it available for TIRF illumination. There are other means of attaching the tape such as running it along the metal oxide layer and folding it back around the ends. The method of attaching the tape does not matter to the function of the sensor, provided that the edge of the plate will permit TIRF illumination, should this type of illumination be used during analysis. Shown below the slide is the structure of the conductor and the gasket. Basically, each has a rectangular shape that enables it to contact the conducting tape without blocking the ability of the user to observe the contents of the sensor, e.g., tissue sections.

FIG. 1C shows a side view of the sensor. FIG. 1C shows an end view of the sensor device 100. Sensor device 100 comprises tissue sections or other analytes 101, brass or other conductor 102, conducting tape 103, ITO or SnO2 coated slides 104, gasket insulator 105, matrix (including buffers) 106, microscope objective 107, CCD camera or other detector 108, and voltage generator 109.

Note that the conducting tape is shown as in a semi-transparent fashion. It does not cover the edge of the sensor plates (slides) for most of the length of the sensor. This is the portion of the sensor that will be used for TIRF illumination, should the illuminator described later be used for visualization of the analytical results. Several different types of visualization can be used, as noted in the text.

FIG. 2 shows the molecular beacon for β-actin. FIG. 2 illustrates the base sequence for a molecular beacon that can be used to recognize β-actin that was purchased from IDT DNA technologies. It contains a rhodamine red fluorophore at its 5' end that is quenched by a black hole 2 quencher at its 3' end in the absence of β-actin. The beacon contains a biotin moiety attached to thymidine that was introduced during synthesis and that enables the beacon to be bound tightly to streptavidin. 5' Rhodamine-red-CAC-CGC-TAG-ATG-GGC-ACA-GTG-TGG-GTG-ACG-CGG-TG-BlkHoleQ2-3'.

FIG. 3 shows the steps in the preparation of biotinylated sensor surfaces. The Steps in the preparation of biotin albumin coated sensor surfaces are: (1) Clean ITO slides in $H_2O$/$H_2O_2$/$NH_3$ (10:2:0.6) 55° C. 75 minutes; (2) Bake slides in vacuum oven 165° C. 150 minutes; (3) Cool with dry nitrogen and coat with SigmaCote; (4) Coat slide with 0.05% bovine serum albumin-biotin (BSA-B) overnight; (5) Wash in phosphate buffered saline (PBS) thoroughly; (6) Coat BSA-B treated slide with streptavidin 0.1 mg/ml 60 minutes; (7) Wash in PBS thoroughly; (8) Coat streptavidin treated slide with molecular beacon (0.1 nMole/ml) 60 min; and (9) Wash thoroughly.

FIGS. 4A-4B illustrate the polarization routines. FIG. 4A shows negatively charged oligonucleotides migrating towards the positively charged sensor surface. The routine is suited for a sensor in which molecular beacons are coated to the sensor surface throughout the analysis as in Example 1. Many other modifications of this will work also. Much higher frequencies would normally be employed (i.e., 200,000 Hz). Changes in the frequency, amplitude, and waveform alter the concentration of the oligonucleotide in the vicinity of the sensor surface and can facilitate or hamper hybridization. Use of voltage patterns such as those illustrated here can be used to alter the hybridization as a function of charge and frequency. This can accelerate binding of the analyte to the sensor surface, increase the specificity of binding interactions, and reduce the non-specific binding. FIG. 4B shows the use of a wave form to prevent premature separation of the analyte and the detection reagent (i.e., fluorescent PNA designed to contain a single positive charge). This is a routine suited for a sensor in which molecular beacons are not to the sensor surface and are free during analysis as in Example 2. Many other modifications of this will work also. Note the frequency shown is diagrammatic only. Much higher frequencies would normally be employed (i.e., 200,000 Hz). This step involves substantial oscillations during the binding phase followed by a change to a constant voltage to drive the complex to the anode.

FIGS. 5A-5B illustrate the principle of sensor operation in Example 2. In this mode of operation the fluorescent detection molecule is usually uncharged or contains a small charge that is opposite that of the analyte. FIG. 5A shows formation of the complex. The complex has the charge found on the analyte. Following complex formation, the fluorescent molecule is carried to one electrode, away from the non-bound fluorophore. FIG. 5B shows that during the separation phase, the fluorescent complex migrates to the anode where it would be observed and the fluorescent unbound PNA migrates to the cathode. Its presence at the cathode would make it invisible to an observer viewing the anode with TIRFM.

FIGS. 6A-6B illustrate TIRF illuminator for multiple objectives. FIG. 6A shows a side view with the position of the light source and objective. Illuminator 600 comprises a laser source 601, a lens 602, a cube 603, a prism 604, a focal point located at the junction of the prism and coverslip 605, the surface of the sensor illuminated 606, the tissue sample 607, the surface of the sensor not illuminated 608, the holder 609, and the objective 610.

The surface area illuminated on the sensor would depend on the curvature of the cylindrical element and its distance from the sensor surface. Only the surface facing the sample would elicit fluorescence. A cutoff filter would need to be placed between the sensor and the detector to distinguish light of different colors—for example from different quantum nanodots.

FIG. 6B illustrates the manner in which the illuminator would be mounted on a microscope.

As shown, the illuminator would be held adjacent to the sensor surface such that both would move side to side as a unit. The sensor could be moved forward and backward relative to the illuminator. This would permit different "slices" of the sensor to be observed.

FIGS. 7A-7B illustrate a modification of the sensor that can be used for heating. FIG. 7A is an end view of the sensor and FIG. 7B is a side view of the sensor. The components of this figure are similar to those of FIG. 1. The major differences involve the modifications needed to provide the mechanism for heating. These include the second ITO layer on the sensor slides and the insulation needed to keep the voltage that is added to this layer from interfering with that that controls the operation of the sensor as a measurement device.

FIG. 7A shows an end view of the sensor device 700. Sensor device 700 comprises tissue sections or other analytes 701, brass or other conductor (inner coating) 702, conducting tape 703, ITO or SnO2 coated slides 704, gasket insulator 705, matrix (including buffers) 706, microscope objective 707, CCD camera or other detector 708, voltage generator 709, brass or other conductor (outer coating) 710, and insulating tape 711.

FIG. 7B shows an end view of the sensor device 700. Sensor device 700 comprises tissue sections or other analytes 701, brass or other conductor (inner coating) 702, conducting tape 703, ITO or SnO2 coated slides 704, gasket insulator 705, matrix (including buffers) 706, microscope objective 707, CCD camera or other detector 708, voltage generator 709, brass or other conductor (outer coating) 710, and insulating tape 711.

FIG. 8 illustrates a microtiter well plate design. Microtiter well plate 800 contains a top with pins 801 in electrical contact glued to a bottom 802 to form wells.

Microtiter well plates that contain conducting surfaces can be constructed in a variety of methods. The only requirement is that two electrically conducting surfaces be able to contact fluids within the well. One method of constructing a plate in which all the wells will be at the same potential is shown in this FIG. 8. A plate that is coated with ITO or other conducting material is used as the base of the microtiter well plate. A molded plastic adapter that forms the individual wells is glued to the metal surface of the plate. The lower part of the top of the plate is made to contain pins that are fabricated from plastic or other convenient material and these are coated with ITO or other metal by a sputtering process. Closure of the plate brings the metal coated pins in contact with fluids in the plate, which are in contact with the metal coated surface on the bottom of the plate. Electrodes are glued to the top and bottom coating and used to create an electrical potential in the well.

In this arrangement, each well will be at the same electrical potential. An alternate mode of constructing the plate top can be used to create plates in which the electric potential in each well can be controlled separately. One way of doing this is to use a top that lacks a conductive layer. A separate wire is inserted through the top into each well. When the microtiter plate is closed, the wire will make electrical contact with the wells.

It should also be noted that it is not necessary for the top of the microtiter plate to contain electrodes. To prepare a device that can be used in an open format, an electrically conducting surface is sputtered on the molded plastic layer that is used to form the walls of the wells to completely coat its inside and outside surfaces. An insulating layer is then coated on the bottom of this molded piece before it is glued to the metal-coated bottom.

FIG. 9A illustrates the overall design of the polymer-based device, which is shown in an expanded schematic form. The following components are present and identified by number. Other variations of this design are possible, however, and these are indicated by the word "optional" associated with the component. The presence of these components can facilitate the analysis but are not absolutely required for analysis. Items 1, 2, 3, and 4 can be combined into a single device termed the anode assembly. Items 6, 7, 8, and 9 can be combined into a single device termed the cathode assembly. These items can be in contact with one another or separated by a fluid during operation of the device. Note that the stippling used to mark each portion of the sensor is not intended to imply that the compositions of these portions of the sensor need to be identical. Note also that the thickness of each layer can differ and that it is not necessary to make them of equal thickness. In fact, it is often beneficial to make them of different thickness.

1. Electrode and electrode holder
2. Spacer to separate electrode and holder from optical surface (optional depending on the design of the electrode holder). This can be made of a hydrogel, sintered polypropylene, or other porous substances.
2a. Semi-permeable membrane to trap analytes
3. Polymer or other material used for optical analysis
4. Polymer or other material to used as a spacer and to facilitate mixing—separates optical analysis surface from sample.
5. Sample
6. Polymer or other material used as a spacer (optional, permits additional analyses)
7. Polymer or other material used as a spacer (optional, permits additional analyses)
8. Spacer to separate electrode and holder from optical surface (optional depending on the design of the electrode holder). This can be made of a hydrogel, sintered polypropylene, or other porous substances.
9. Electrode and holder.

FIG. 9B illustrates the device as it is being assembled. The tissue section (5) is placed on either the lower or upper assembly, which are composed of components 1, 2, 3, and 4 and of components 6, 7, 8, and 9, respectively. It is usually most convenient to place it on the anode assembly as shown here, but it does not matter which is used first. Then the other assembly is added to complete the device, which has all 9 components as shown. Note that the components are identified in FIG. 9A.

FIG. 9C illustrates the device as it is being used during electrophoresis. A convenient means of doing the electrophoresis is to take the assembled components shown in FIG. 9B and slide them into a box that contains the connections that enable a voltage to be placed on the electrodes (items 1 and 9 in diagrams 9A and 9B). This holds the sensor device together and can be up-ended. This keeps any bubbles that arise during electrolysis of water from interfering with analysis. The box contains electrodes that make electrical contacts with those on the outer edges of the sensor. As noted later, it is also possible to eliminate the electrodes on the sensor or the box, but not both. Note, the components can be identified by reference to FIG. 9A. Note also, the electrophoresis chamber is made from Plexiglas or similar plastic and contains two vertical triangular pieces of plastic along the edges denoted "Anode" and "Cathode" that prevent the sensor sandwich (i.e., the stack at the left) from being inserted into it in an incorrect orientation or if it has been assembled incorrectly from two cathode assemblies or two anode assemblies.

FIG. 9D illustrates the construction of the anode (component #1 plus component #2) and cathode (component #8 plus component #9). Both the anode and the cathode can be constructed in the same fashion but each has a different corner cutout as shown in the panels at the left, which prevents them from being inserted into the electrophoresis box (FIG. 9C) in an improper orientation. The sole function of these components is to deliver a voltage across the device in a way that does not disrupt the functions of the gels. The solid gray rectangles indicate the metal electrodes and the crosshatched areas indicate the plastic holder. Together, these correspond to components #1 and #9 in FIG. 9A. The plastic holder is made from a square rod that is cutout to accommodate the metal electrode and the sintered polyethylene frit that is stippled in these diagrams and corresponds to components #2 and #8 in FIG. 9A. The left panel illustrates cross sections of the device through the position noted on the figure as they are modified for the anode (lower diagram) and cathode (upper diagram). The second, third, and fourth panels illustrate longitudinal views from the side, front, and back. (The front is the surface that is in contact with the polymer or a dialysis membrane.) Note that the device is filled with fluid before the frit is glued to the top. This creates an air space at the top of the device that permits gasses to be vented caused by electrolysis during electrophoresis. Note that the cap is surrounded by a heat shrink plastic coating (indicated by the black square dots) that is removed during use of the device. This prevents loss of fluid from the device during storage. Passage of fluid through the other frit is blocked by the presence of components (i.e., #2a and #3 or #7, FIG. 9A), which contact it. As a result, there is no need for the technician or other operator to add fluid to the device during its use. Small amounts of detergents can be used to facilitate wetting of the frit although this is usually not needed. Devices can also be constructed in which the fluid is added by the operator at the time of use. Note that in this case, it is not necessary that the anode or cathode components #1 and #9 contain the electrode (solid gray rectangles). The anode and cathode components can be located in the electrophoresis box to which the operator would add the buffer fluid. In this case, it would also not be essential to add the frit or the temporary seal to the top of the device as shown in the longitudinal views in this figure.

FIG. 9E illustrates the construction of the anode and cathode assemblies. The polymeric gels that are to be included into the assembly are prepared separately and cut into the size that will be used in the device. This size should be at least equal to or larger than the tissue sections or other materials to be analyzed. Indeed, it is usually preferable to make these 25% larger than the expected tissue sections to facilitate placing the sections on the device during operation. Since it is possible to build the device so that multiple sections can be observed at the same time, the size of the gel pieces to be used will depend on the number of sections that are to be placed on the device and subjected to electrophoresis at the same time. The final assembly step is to hermetically seal the device in a watertight bag along with a few drops of water to compensate for any evaporation. A small piece of moist paper towel can also be used for this purpose.

FIG. 9F illustrates the mounting of the "exposed" sensor sandwich on the camera. The anode and the sintered polyethylene component are removed. This is easily done by placing a small spatula between the corners of component #2 and the dialysis tubing or component #3 and twisting to dislodge the anode. Care should be taken not to dislodge the dialysis tubing or component #3. The remainder of the sandwich is placed on a fiber optic window or a fiber optic taper that is coupled to the chip of a sensitive CCD camera (11). The sample will be detected by total internal reflection fluorescence (TIRFM) using an illumination system based on a laser or other illumination device that illuminates component #3. Although not depicted, the illumination is designed such that the entire area of the face of this component is illuminated. This will enable the CCD camera to record an image of the entire section at one time. The resolution of the camera will depend on the number of pixels on its chip, the size of each pixel, and the sizes of the fibers that are used to make the fiber optic window or taper. A resolution of between 20-50 µm is sufficient for the analysis since this will enable the determination of the RNA to an area of 2-3 cells. This information is transferred to a computer for data processing. The cathode can also be removed if desired, but this is not essential until the tissue slice is to be examined by regular microscopy. This will often depend on what is seen from the fluorescent image.

FIG. 10A illustrates the migration of PNA labeled with a fluorophore (PNA*) when it is free and bound to RNA in the sensor apparatus. Note that the complex will not pass through the dialysis membrane (component #2a) due to the limitation of the pore size. The pore size of component #3 can also be kept small such that the RNA/PNA* complex will not penetrate through it in which case the dialysis membrane component (i.e., #2a) is not essential and would not be used. It is critical that the uncomplexed PNA* not enter the compartment created by component #3, however, since this would create an unacceptably high background in the device. Thus, it is important to use PNA* that are positively charged in the vicinity of component #3 so that they migrate away from this component and from its surface. Since the analysis will take advantage of the principle of total internal reflection fluorescence (TIRF), in which materials that are outside the standing evanescent wave that is created by illumination of component #3, the distance of the PNA* from component #3 need be only a few hundred nanometers.

Figure 10B:
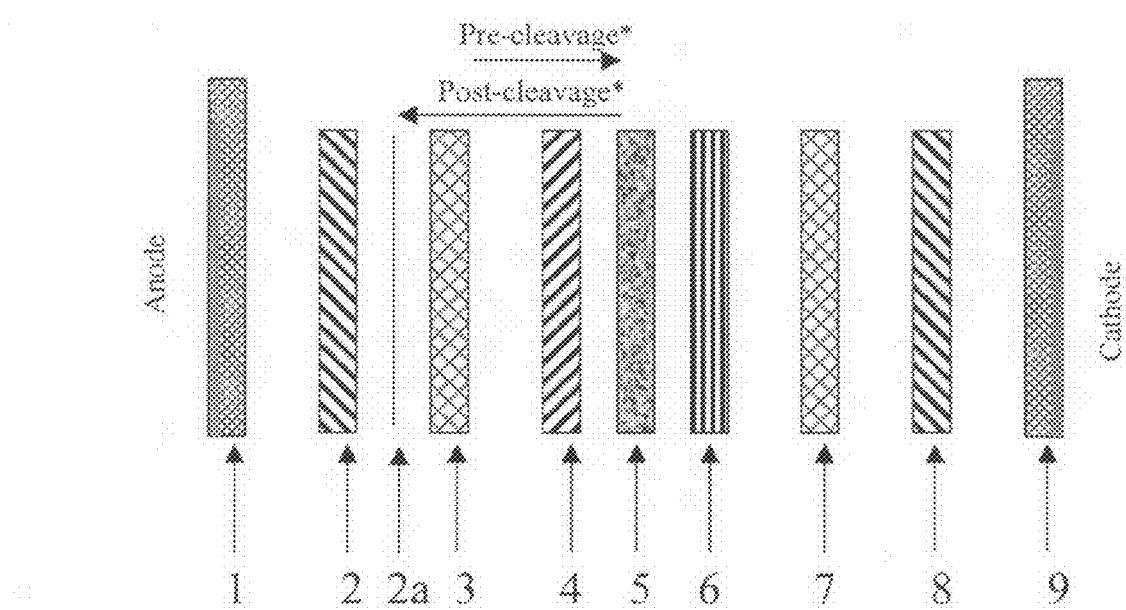

FIG. 10B illustrates the migration of a fluorescent charged detection agent before and after its charges have been removed by an enzyme or a reaction with materials in or released from the tissue section. When the unreacted detection is positively charged and the reaction causes it to become negatively charged by removing its positively charged residues such as lysine or arginine amino acids, this would change the charge on the detection agent and cause it to migrate towards component #3 as shown. Furthermore, the fluorescent detection agent could be designed such that removal of the charged portion exposes a binding site that will interact with a site or sites coupled to component #3. Thus, it can be seen that a change in the charge of a detection agent or the formation of a complex that has a different charge from the uncomplexed detection agent can be used for the detection of analytes, including those that are spatially organized such as would occur in tissue sections.

FIG. 11 illustrates design considerations for component #3. The cross-linking of the hydrogel in component #3 should depend on the analysis. In the case of analytes such as RNA, it is often useful to employ a high cross-linking, which will keep the refractive index high and cause the hydrogel to behave as a semi-permeable barrier to RNA, keeping it on the surface that faces component #4. Also, in the case of negatively charged analytes such as RNA that are to be detected with positively charged reagents such as PNA that contain positively charged residues, the surface of component #3 can be cross-linked with a positively charged material that will repel the detection reagent unless it is bound to the negatively charged RNA. This will also be facilitated by using a buffer that has a pH that is lower than that of the pI of the PNA. The surface of component #3 that faces component #2 should be hydrophilic to make it attract an aqueous layer that can be used to separate it from the fiber optic.

FIG. 12A illustrates the arrangement of the system used to illuminate component #3 (or component #7, when used). Component #3 is placed on top of the optical fiber such that a thin water or buffer layer separates the two. This is needed to cause total internal reflection of the illumination beam (heavy black arrow). Fluorescence (thin downward pointing arrow) passes through the buffer layer and through a filter (if present) that is designed to block scattered illumination. This illumination should be minimal when the interfaces of components #3 and #4 and the water and component #3 are smooth and clean. Use of a cutoff filter can reduce scattered light but will make it more difficult to measure the emission at more than one excitation wavelength unless a filter wheel assembly is employed. A useful way to increase the signal to noise ratio is to illuminate the sample with polarized light and to block the transmission of light having this polarization with a filter at the location shown. Note that the laser beam should be compressed in the vertical direction and expanded in the horizontal direction to enable illumination of the entire surface of component #3. This will permit an image of the analyte in the entire tissue section depicted as component #5 is to be determined at one time. Note that the size of the sensor as reflected in component #3 should be slightly smaller than the size of the image that is taken from the fiber optic. This is to permit a low-resolution image to be taken of the outline of component #3. This can be used to align the fluorescence image with that of the tissue section when the sensor sandwich is transferred to a standard inverted microscope for observation through an objective.

Figure 12B:
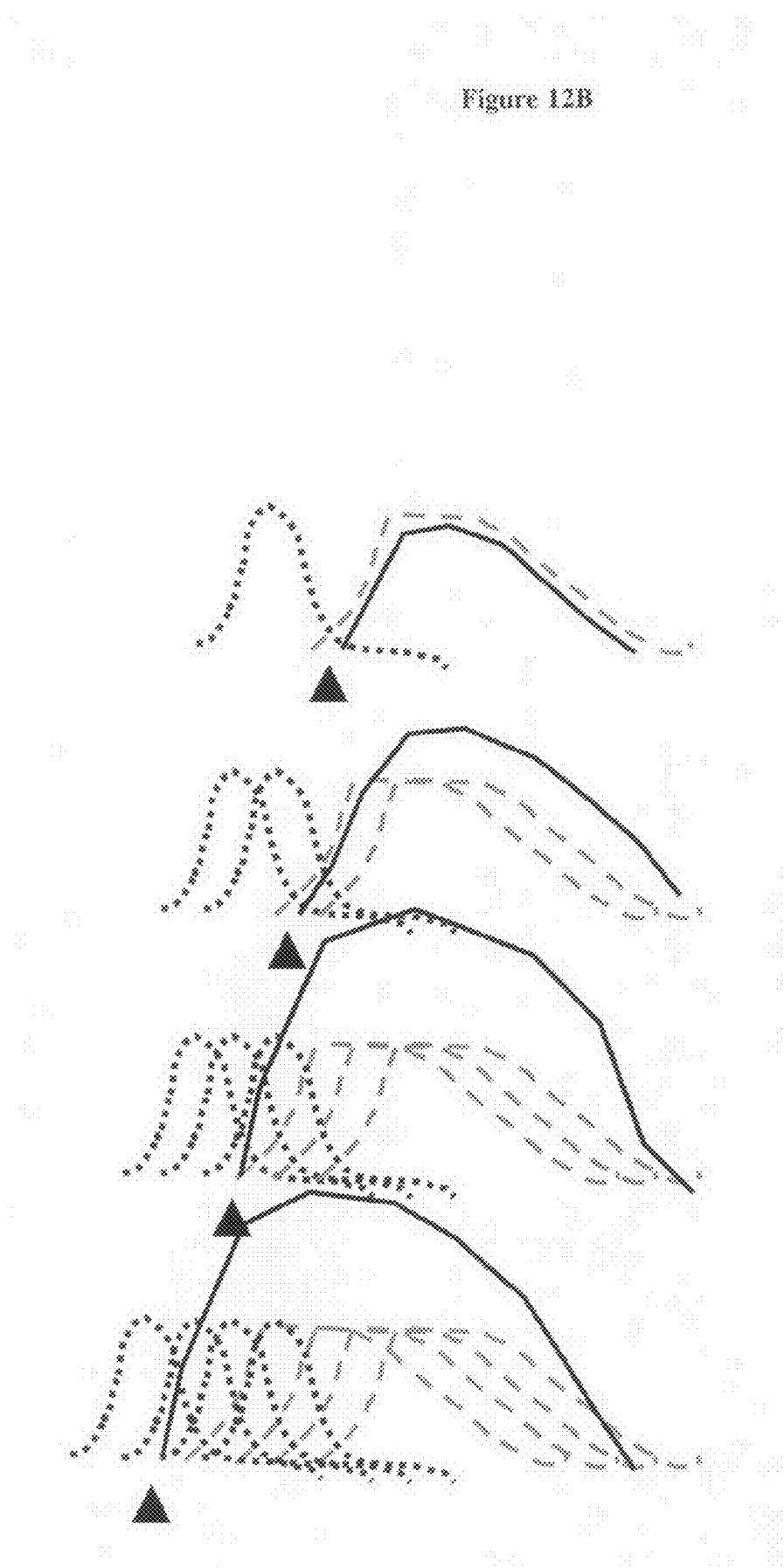
FIGS. 12A-12D illustrate the illumination of the system.

FIG. 12B illustrates the illumination used to distinguish colors. The filled triangles indicate the relative wavelength used for illumination with the right most position indicating longer wavelengths and the left most position indicating shorter wavelengths. Component #3 is first illuminated with the longest wavelength and the fluorescence measured. It is then illuminated sequentially with increasingly short wavelengths as represented by the panels going from the top of the figure to the bottom of the figure. The fluorescence excitation spectrum is represented by the dotted black lines in each panel. The fluorescence emission spectrum is represented by the dashed gray lines in each panel. The fluorescence that is measured is represented by the solid black lines. As is represented schematically here, the increase in total fluorescence represented by the black lines at increasingly shorter wavelengths can be resolved mathematically by "subtracting" the fluorescence from each of the subsequent lines. This is done via a matrix algebra approach in which the fluorescence excitation and emission standards is known at each wavelength employed.

Figure 12C:
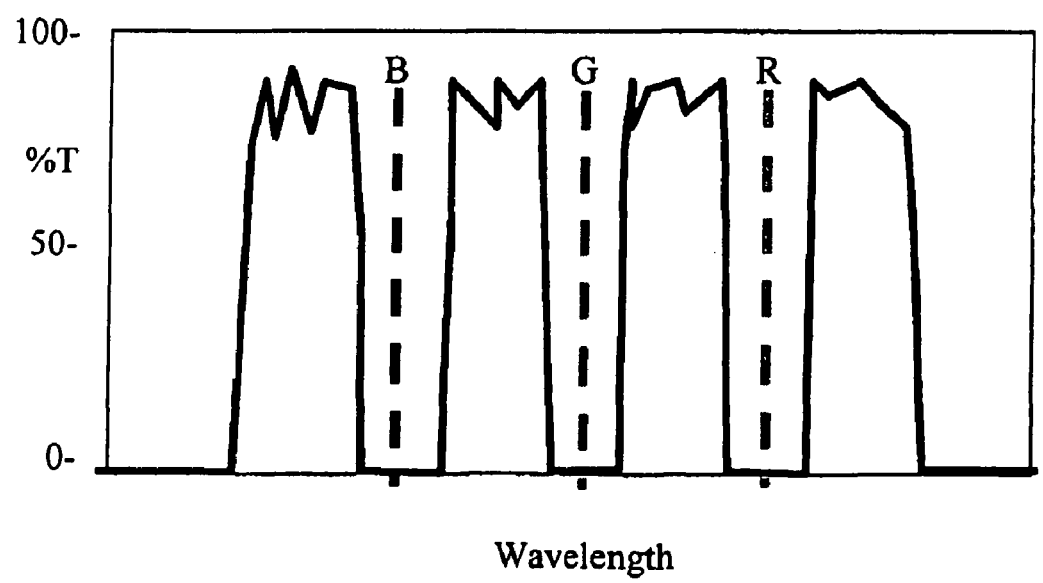
Figure 12:
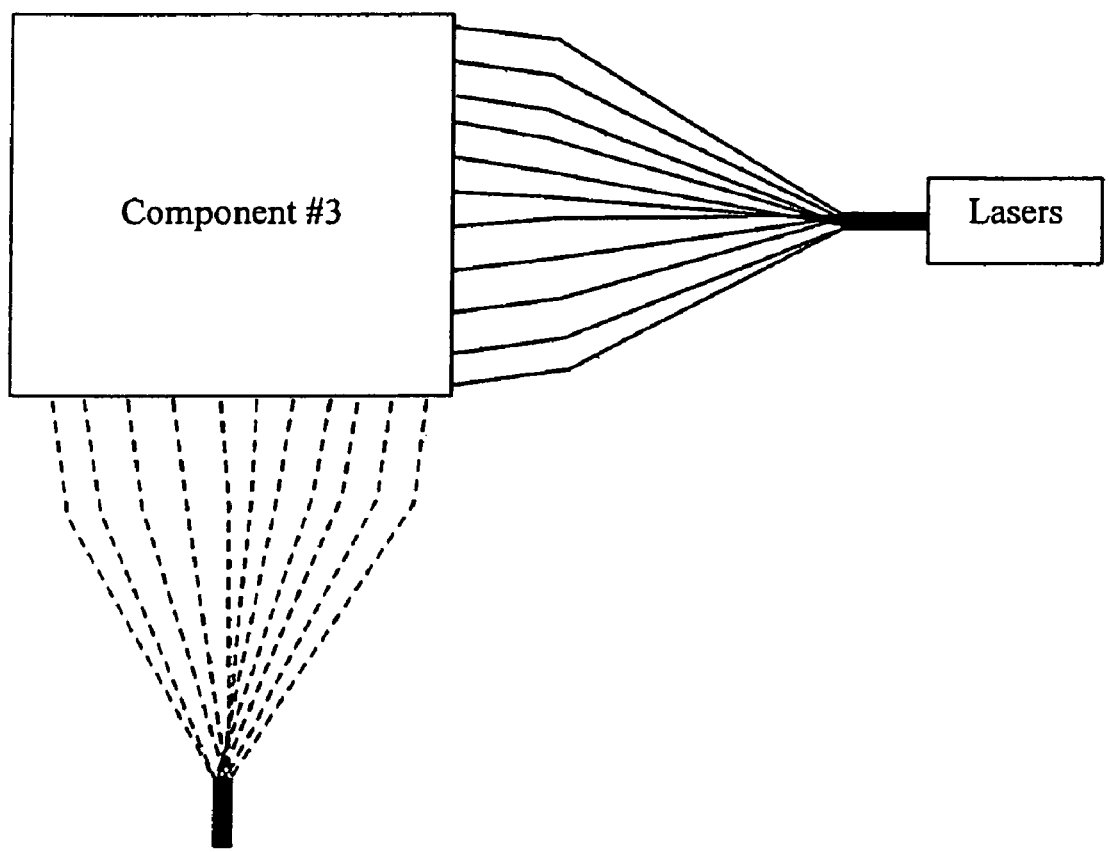

FIG. 12C illustrates a preferred type of filter that can be used in the device to permit distinguishing colored fluorophores, if it is necessary to reduce the amount of scattered light. This type of filter is known as a multi-band pass filter because it has the ability to block wavelengths of several laser lines such as those indicated by the broken lines under the letters B, G, and R. As a result scattered light that is used to excite the sample by total internal reflection will be prevented from reaching the fiber optic window or fiber optic taper and will not interfere with analysis. In the diagram below, the B, G, and R refer to the maximum emission of blue, green, and red lasers respectively. Since this is an emission filter, it would also reduce the amount of fluorescent signal but it would increase the signal to noise ratio by reducing the amount of scattered light even further. A second type of filter that could be used blocks polarized light. Since light emitted by fluorophores that are illuminated by evanescent light will not have the same polarity as the light used to illuminate component #3, the light they emit will not be blocked by a filter that is designed to block polarized light that is used for illumination. Therefore, the polarization filters will block the light scattering much more effectively than they will block the fluorescent signal. This will raise the signal to noise ration. Finally, a third means of distinguishing color in this device is to employ fluorophores that are photobleached at different rates. By monitoring the change in signal as a function of time, it is possible to distinguish each of the fluorophores. This also permits use of fluorophores that have nearly identical emission spectra. Thus, fluorescence from a fluorophore that is readily photobleached will decay much more rapidly than that from a fluorophore that is more stable. When this type of analysis is employed, it is desirable to use label the more abundant analytes with the fluorophore that is the least stable.

FIG. 12D illustrates a preferred mode for illuminating the sample. Illumination of the sample can be accomplished using a fiber optic bundle that is divided into fibers that are held in a linear array next to component #3 as shown here looking down at component #3. The diagram also shows that more than one fiber bundle can be used if desired. This can be connected to the same laser(s) indicated on the figure, or it can be connected to different lasers. Note that the number of fibers shown on this diagram is for illustration purposes only. There can be fewer or, more likely, many more fibers. The diameter of the fibers (core plus cladding) should be less than the thickness of component #3. The numerical aperture of the fibers should be chosen to be smaller than that which violates the principle of total internal reflection. This will depend on the refractive index of component #3 and the refractive indices of the materials above and below component #3 that contact it. This angle can be calculated from the Snell equation.

One aspect of the invention provides hydrogels similar to those used to make contact lenses that can be used in a sensor because the hydrogels are suitable for electrophoresis and optical refraction and capture of reagents. The other aspect of the invention is the sensor itself and will depend on how the sensor is used. The sensor is designed to be user friendly in that the user does not need to add any fluids. For this reason, the electrodes need to be built into the sensor. In other uses, the user can add the fluids. In this case the electrodes do not need to be built into the sensor per se, but can be built into the electrophoresis box. FIG. 9 shows them simply to make electrical contact with the electrodes in the sensor device. If one were to add fluid to the box, then the electrodes would not need to be in the sensor. Another aspect of the invention is that the charge of the material doing the analysis is altered during analysis. This change in charge occurred because the detection agent became bound to the analyte (i.e., the PNA are designed to be positively charged and the complex with RNA will be negatively charged). It is also possible for the detection agent to be modified by the analyte and to have its charge changed. Thus, an enzyme that cuts off a positively charged portion of the analyte can alter its charge. This will cause it to migrate towards the anode if this results in a change from positive to negative. This can also be used to create a new binding surface on the analyte as well.

The word "bound" reflects the idea of "change" as well as "binding." Interaction of the detection reagent with the analyte leads to a change in the direction of its migration in an electric field. Electrodes do not need to be attached to the sensor per se unless the device is to be constructed such that the user does not need to add fluid. A spacer would still be required to keep the component #3 from touching the electrode to permit bubbles to escape the device. The device as shown is useful for analyses that are located at different spatial positions in an analyte such as a tissue section.

REFERENCES (1) International Human Genome Sequencing Consortium. Initial sequencing and analysis of the human genome. Nature 2001; 409:860-921.

(2) Venter C J et al. The sequence of the human genome. Science 2001; 291:1304-1351.

(3) Moseley M R. Current trends in differential expression proteomics: isotopically coded tags. Trends in Biotechnology 2001; 19:S10-S16.

(4) Dhanasekaran S M, Barrette T R, Ghosh D, Shah R, Varambally S, Kurachi K, Pienta K J, Rubin M A, Chinnaiyan A M. Delineation of prognostic biomarkers in prostate cancer. Nature 2001; 412(6849):822-826.

(5) 't Veer L J, Dai H, van de Vijver M J, He Y D, Hart A A, Mao M, Peterse H L, van der K K, Marton M J, Witteveen A T, Schreiber G J, Kerkhoven R M, Roberts C, Linsley P S, Bernards R, Friend S H. Gene expression profiling predicts clinical outcome of breast cancer. Nature 2002; 415 (6871):530-536.

(6) Monni O, Hyman E, Mousses S, Barlund M, Kallioniemi A, Kallioniemi O P. From chromosomal alterations to target genes for therapy: integrating cytogenetic and functional genomic views of the breast cancer genome. Semin Cancer Biol 2001; 11(5):395-401.

(7) Mousses S, Wagner U, Chen Y, Kim J W, Bubendorf L, Bittner M, Pretlow T, Elkahloun A G, Trepel J B, Kallioniemi O P. Failure of hormone therapy in prostate cancer involves systematic restoration of androgen responsive genes and activation of rapamycin sensitive signaling. Oncogene 2001; 20(46):6718-6723.

(8) Quarmby S, West C, Magee B, Stewart A, Hunter R, Kumar S. Differential expression of cytokine genes in fibroblasts derived from skin biopsies of patients who developed minimal or severe normal tissue damage after radiotherapy. Radiat Res 2002; 157(3):243-248.

(9) Rew DA. DNA microarray technology in cancer research. Eur J Surg Oncol 2001; 27(5):504-508.

(10) Simpson R J, Dorow D S. Cancer proteomics: from signaling networks to tumor markers. Trends in Biotechnology 2001; 19:S40-S48.

(11) Liggett S B, Caron M G, Lefkowitz R J, Hnatowich M. Coupling of a mutated form of the human beta 2-adrenergic receptor to Gi and Gs. Requirement for multiple cytoplasmic domains in the coupling process. J Biol Chem 1991; 266:4816-4821.

(12) Tsuji A, Sato Y, Hirano M, Suga T, Koshimoto H, Taguchi T, Ohsuka S. Development of a time-resolved fluorometric method for observing hybridization in living cells using fluorescence resonance energy transfer. Biophys J 2001; 81(1):501-515.

(13) Liu X, Tan W. A fiber-optic evanescent wave DNA biosensor based on novel molecular beacons. Anal Chem 1999; 71(22):5054-5059.

(14) Zhuang X, Bartley L E, Babcock H P, Russell R, Ha T, Herschlag D, Chu S. A single-molecule study of RNA catalysis and folding. Science 2000; 288(5473):2048-2051.

(15) Lakowicz J R. Principles of fluroescence spectroscopy. second ed. New York: Kluwer Academic/Plenum Publishers, 1999.
(16) Tyagi S, Kramer FR. Molecular beacons: probes that fluoresce upon hybridization. Nat Biotechnol 1996; 14:303-308.
(17) Basile, A., A. Giuliani, G. Pirri, and M. Chiari. 2002. Use of peptide nucleic acid probes for detecting DNA single-base mutations by capillary electrophoresis. *Electrophoresis* 23:926-929.
(18) Chen, C., Y. K. Hong, S. D. Ontiveros, M. Egholm, and W. M. Strauss. 1999. Single base discrimination of CENP-B repeats on mouse and human Chromosomes with PNA-FISH. *Mamm. Genome* 10:13-18.
(19) Hirano, H., H. Kawasaki, and H. Sassa. 2003. Two-dimensional gel electrophoresis using immobilized pH gradient tube gels. *Electrophoresis* 21:440-445.
(20) Jansen, K. and E. Richelson. 2000. Detection of peptide nucleic acids in tissue extracts of treated animals by gel mobility shift assay. *J. Biochem. Biophys. Methods* 42:31-34.
(21) Kim, D. H., Y. K. Hong, M. Egholm, and W. M. Strauss. 2001. Non-disruptive PNA-FISH protocol for formalin-fixed and paraffin-embedded tissue sections. *BioTechniques* 31:472, 475-472, 476.
(22) Pokidysheva, E. N., I. A. Maklakova, Z. M. Belomestnaya, N. V. Perova, S. N. Bagrov, and V. I. Sevastianov. 2001. Comparative analysis of human serum albumin adsorption and complement activation for intraocular lenses. *Artivicial Organs* 25:453-458.
(23) Pokidysheva, E. N., I. A. Maklakova, Z. M. Belomestnaya, N. V. Perova, S. N. Bagrov, and V. I. Sevastianov. 2003. Comparative analysis of human serum albumin adsorption and complement activation for intraocular lenses. *Artif. Organs* 25:453-458.
(25) Ray, R. and B. Norden. 2000. Peptide nucleic acid (PNA): its medical and biotechnical applications and promise for the future. *FASEB J.* 14:1041-1060.
(26) Zuo, X. and D. W. Speicher. 2002. Comprehensive analysis of complex proteomes using microscale solution isoelectrofocusing prior to narrow pH range two-dimensional electrophoresis. *Proteomics* 2:58-68.

Throughout this application, various publications have been referenced. The disclosures in these publications are incorporated herein by reference in order to more fully describe the state of the art.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A method for detecting an ionic analyte in a sample in which an analyte is bound to a detection reagent to form a bound complex, comprising the steps of:
   (A) providing a sensor device comprising:
   (a) a sample (5) comprising an ionic analyte and a detection reagent in a conductive fluid, wherein the detection reagent has a net charge different from the analyte;
   (b) a first permeable polymeric hydrogel plate (3) and a first spacer plate (8), which plates provide a compartment for the sample;
   (c) an anode (1) juxtaposed to the outside of the first hydrogel plate and not in contact with the sample;
   (d) a cathode (9) juxtaposed to the outside of the first spacer plate and not in contact with the sample;
   (e) a voltage generator (10) to apply an electric potential to the anode and cathode; and
   (f) a detector (11); and
   (B) adding the ionic analyte and detection reagent in the conductive fluid to the compartment;
   (C) applying an electrical potential via the voltage generator; and
   (D) detecting via the detector the bound complex formed from the analyte because the bound complex has a charge that causes it to migrate in a direction opposite from that of the unbound analyte when the electric potential is applied.

2. The method according to claim 1, wherein the ionic analyte is a gene product in a cell or tissue section sample.

3. The method according to claim 2, wherein the gene product is a nucleic acid or protein.

4. The method according to claim 1, wherein the detection reagent is selected from the group consisting of uncharged peptide nucleic acids, negatively charged peptide nucleic acids, positively charged peptide nucleic acids, peptide nucleic acids labeled with a fluorophore, and peptide nucleic acids in which a phosphate group has been replaced by a sulfate group or a carbonate group.

5. The method according to claim 4, wherein the peptide nucleic acid has a hairpin conformation.

6. The method according to claim 1, wherein the first permeable polymeric hydrogel plate comprises a hydroxyethylmethacrylate or a hydroxyethylmethacrylate-methacrylic acid.

7. The method according to claim 1, further comprising a second permeable polymeric hydrogel plate (7) juxtaposed between the first spacer plate and the sample.

8. The method according to claim 7, wherein the second permeable polymeric hydrogel plate comprises a hydroxyethylmethacrylate or a hydroxyethylmethacrylate-methacrylic acid.

9. The method according to claim 1, further comprising a second spacer plate (2) juxtaposed between the first permeable polymeric hydrogel plate and the anode.

10. The method according to claim 9, further comprising a semipermeable membrane (2a) juxtaposed between the second spacer plate and the first permeable polymeric hydrogel plate.

11. The method according to claim 7, further comprising a first (4) polymeric plate juxtaposed between the first permeable polymeric hydrogel plate and the sample and a second (6) polymeric plate juxtaposed between the second permeable polymeric hydrogel plate and the sample, wherein the first and second polymeric plates have a lower refractive index than that of the first and second permeable polymeric hydrogel plates, respectively.

12. The method according to claim 11, wherein the first and second polymeric plates comprise a polyacrylamide, an agarose gel, a hydroxyethylmethacrylate, or a hydroxyethylmethacrylate-methacrylic acid.

13. The method according to claim 1, wherein the detector is a fluorescence, luminescence, colorimetry, or total internal reflection illumination detector.

14. The method according to claim 1, wherein the detector detects by phase contrast microscopy, bright field microscopy, darkfield microscopy, differential interference contrast microscopy, confocal microscopy, or epifluorescence microscopy.

15. The method according to claim 1, wherein the electrical potential is applied perpendicular to the plates and is constant or varied such that the overall effect is to have each plate have a net charge, such that charged analytes in the sample will migrate to one plate.

16. The method according to claim 1, wherein the electrical potential is applied perpendicular to the plate ands is alternated such that there is no net charge on either plate, such that charged analytes will oscillate back and forth in the central space away from either plate where they interact with the detection reagent.

17. The method according to claim 1, wherein the detection reagent is a molecular beacon.

18. The method according to claim 1, wherein a second molecular beacon is employed as an internal control.

19. The method according to claim 18, wherein a first molecular beacon is employed to detect a control gene product and a second molecular beacon is employed to detect a gene product of experimental or diagnostic interest, wherein the first and second molecular beacons are each labeled with a different fluorophore that emits at a different wavelength so that the first and second molecular beacons can be simultaneously analyzed.

* * * * *

SEQUENCE LISTING

```
<160> NUMBER OF SEQ ID NOS: 1

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caccgctaga tgggcacagt gtgggtgacg cggtg                               35
```